United States Patent
Simaan et al.

(10) Patent No.: US 9,089,354 B2
(45) Date of Patent: Jul. 28, 2015

(54) DEVICES, SYSTEMS AND METHODS FOR MINIMALLY INVASIVE SURGERY OF THE THROAT AND OTHER PORTIONS OF MAMMALIAN BODY

(71) Applicant: The Johns Hopkins University, Baltimore, MD (US)

(72) Inventors: Nabil Simaan, Baltimore, MD (US); Russell H. Taylor, Severna Park, MD (US); Paul Flint, Baltimore, MD (US); Gregory Chirikjian, Towson, MD (US); David Stein, Succasunna, NJ (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 13/740,825

(22) Filed: Jan. 14, 2013

(65) Prior Publication Data
US 2013/0197539 A1    Aug. 1, 2013

Related U.S. Application Data

(63) Continuation of application No. 10/850,821, filed on May 21, 2004, now Pat. No. 8,365,633.

(60) Provisional application No. 60/472,168, filed on May 21, 2003.

(51) Int. Cl.
*A61M 31/00* (2006.01)
*A61B 19/00* (2006.01)
(Continued)

(52) U.S. Cl.
CPC ............. *A61B 19/2203* (2013.01); *A61B 19/22* (2013.01); *A61B 19/26* (2013.01); *A61B 17/24* (2013.01); *A61B 17/3421* (2013.01); *A61B 19/5212* (2013.01); *A61B 2017/003* (2013.01);
(Continued)

(58) Field of Classification Search
USPC .......... 74/490.01, 490.04; 600/141, 146, 149; 606/1
See application file for complete search history.

(56) References Cited

U.S. PATENT DOCUMENTS

3,269,017 A    8/1966 Stewart
3,557,780 A *  1/1971 Sato .............................. 600/141
(Continued)

FOREIGN PATENT DOCUMENTS

DE    41 02 211 A1    8/1991
EP    0924846 A2    6/1999
(Continued)

*Primary Examiner* — William C Joyce
(74) *Attorney, Agent, or Firm* — Mintz Levin Cohn Ferris Glovsky and Popeo, P.C.; Peter F. Corless

(57) ABSTRACT

Featured are systems, devices and apparatuses for use in minimally invasive surgical, diagnostic or therapeutic methods and/or techniques, in particular methods and/or techniques for a mammalian throat. In particular embodiments, a dexterity apparatus including one or more dexterity devices is featured, where each of the dexterity devices comprises surgical tools and each is configured and arranged with end-tip dexterity for enhanced manipulation. A portion of the dexterity devices is snake like, which is re-configurable (i.e., can be bent) so as to in effect maneuver the surgical tool and put the tool in a desired position with respect to the surgical site. Another portion of the dexterity device includes the surgical tool thereby providing the capability of performing surgical actions such as sewing, gripping, soft tissue manipulation, cutting and suction of saliva, blood and other materials from the surgical site.

20 Claims, 11 Drawing Sheets

(51) Int. Cl.
*A61B 17/24* (2006.01)
*A61B 17/34* (2006.01)
*A61B 17/00* (2006.01)

(52) U.S. Cl.
CPC . *A61B 2017/3445* (2013.01); *A61B 2019/2211* (2013.01); *A61B 2019/2223* (2013.01); *A61B 2019/2234* (2013.01); *A61B 2019/2238* (2013.01); *A61B 2019/2242* (2013.01)

(56) References Cited

U.S. PATENT DOCUMENTS

| | | | |
|---|---|---|---|
| 5,649,955 | A | 7/1997 | Hashimoto et al. |
| 6,352,503 | B1 | 3/2002 | Matsui et al. |
| 6,802,319 | B2 | 10/2004 | Stevens et al. |
| 6,858,005 | B2 * | 2/2005 | Ohline et al. ............... 600/141 |
| 6,899,704 | B2 | 5/2005 | Sterman et al. |
| 2002/0120252 | A1 | 8/2002 | Brock et al. |

FOREIGN PATENT DOCUMENTS

| | | |
|---|---|---|
| JP | 08-033644 A | 2/1996 |
| JP | 11-198069 A | 7/1999 |
| JP | 2000-033071 A | 2/2000 |
| JP | 2000-037348 A | 8/2001 |
| WO | WO-95/18311 A1 | 7/1995 |
| WO | WO-98/56297 A1 | 12/1998 |
| WO | WO-02/065933 A2 | 8/2002 |

* cited by examiner

DEVICES, SYSTEMS AND METHODS FOR MINIMALLY INVASIVE SURGERY OF THE THROAT AND OTHER PORTIONS OF MAMMALIAN BODY

This application claims the benefit of U.S. Provisional Application Ser. No. 60/472,168 filed on May 21, 2003, the teachings of which are incorporated herein by reference. This application is also a continuation of U.S. Pat. No. 8,365,633, which issued on Feb. 5, 2013, and which also claimed the benefit of U.S. Provisional Application Ser. No. 60/472,168, and the teachings of U.S. Pat. No. 8,365,633 are also incorporated herein by reference.

STATEMENT REGARDING FEDERALLY-SPONSORED RESEARCH

The present invention was supported by grants from the National Science Foundation (NSF) under Engineering Research Center Grant No. EEC9731478, NSF Grant No. IIS9801684. The U.S. Government may have certain rights to the present invention.

FIELD OF INVENTION

The present invention relates to devices, systems and surgical techniques for minimally invasive surgery and more particularly to minimally invasive devices, systems and surgical techniques/methods associated with treatment, biopsy and the like of the throat and related elements or structures thereof (e.g., larynx, thorax).

BACKGROUND OF THE INVENTION

Minimally invasive surgery is a surgical approach aimed at reducing the healing time and trauma to a patient as a result of performing surgery on internal organs. In this approach, the treated internal organs are accessed through a small number of incisions in the patient's body. In particular, cannulas or sleeves are inserted through small incisions to provide entry ports through which surgical instruments are passed. Alternatively, access to the area to be treated is obtained using a natural bodily opening (e.g., throat, rectum), a cannula or sleeve is inserted into the bodily opening and the surgical instruments are passed through the cannula/sleeve or the bodily opening and the operable end localized to the treatment site.

The surgical instruments are generally similar to those used in open surgical procedures except they include an extension (e.g., a tubular extension) between the end of the tool entering the surgical field (i.e., the operable end of the tool, instrument or device) and the portion gripped by the surgeon. Because the surgical site or treatment site is not directly visible to the surgeon or other medical personnel when performing a minimally invasive procedure, a visualization tool/guide (e.g., endoscope, laparoscope, laryngoscope, etc.) also is inserted along with the surgical instruments so that, as the surgeon manipulates the surgical instruments outside of the surgical site, he or she is able to view the procedure on a monitor.

The limited motion available at the operable end of current devices, however, creates limitations that necessarily limit that which can be accomplished with the methods and procedures using current devices and systems. Most instruments or devices are rigid and are limited to motions of four (4) degrees of freedom of motion or less about the incision point and in/out translation. Further, the instruments can limit the surgeon's ability to accurately perceive the force/interaction between the instruments and tissues/organs. Some techniques have been established whereby the location of the incision(s) is optimized so as to in effect counter the limitations imposed by the available movement of a given instrument. This approach, however, does not work for all surgical techniques such as those surgical techniques in which access to the treatment or surgical site is accomplished using an existing bodily opening, such as the throat.

Several approaches to distal tool dexterity enhancement have been reported including designs for catheters or surgical tool manipulation devices based on articulated designs.. Many systems and actuation methods are mainly based on wire actuation or use of wire actuated articulated wrists [G. Guthart and K. Salisbury, "The Intuitive' Telesurgery System: Overview and Application," IEEE International Conference on Robotics and Automation, pp.618-621, 2000; M. Cavusoglu, I. Villanueva, and F. Tendick, "Workspace Analysis of Robotics Manipulators for a Teleoperated Suturing Task," IEEE/RSJ International Conference on Intelligent Robots and Systems, Maui, HI, 2001] and by using Shape Memory Alloys (, bending SMA forceps were suggested for laparoscopic surgery, Y. Nakamura, A. Matsui, T. Saito, and K. Yoshimoto, "Shape-Memory-Alloy Active Forceps for Laparoscopic Surgery," IEEE International Conference on Robotics and Automation, pp.2320-2327, 1995]; an SMA actuated 1 degree of freedom planar bending snake device for knee arthroscopy was described, P. Dario, C. Paggetti, N. Troisfontaine, E. Papa, T. Ciucci, M. C. Carrozza, and M. Marcacci, "A Miniature Steerable End-Effector for Application in an Integrated System for Computer-Assisted Arthroscopy," IEEE International Conference on Robotics and Automation, pp.1573-1579, 1997; and a hyper-redundant SMA actuated snake for gastro-intestinal intervention was described;[D. Reynaerts, J. Peirs, and H. Van Brussel, "Shape Memory Micro-Actuation for a Gastro-Intesteinal Intervention System," *Sensors and Actuators*, vol. 77, pp. 157-166, 1999). A two DoF 5 mm diameter wire-driven snake-like tool using super-elastic NiTi flexure joints also has been described [J. Piers, D. Reynaerts, H. Van Brussel, G. De Gersem, and H. T. Tang, "Design of an Advanced Tool Guiding System for Robotic Surgery," IEEE International Conference on Robotics and Automation, pp.2651-2656, 2003]. Also described is actuation methods and systems that use Electro-Active Polymers (EAP) (e.g., see A. Della Santa, D. Mazzoldi, and DeRossi, "Steerable Microcatheters Actuated by Embedded Conducting Polymer Structures," *Journal of Intelligent Material Systems* and *Structures*, vol. 7, pp. 292-300, 1996). These designs however, have a number of limitations. The articulated designs limit downsize scalability and complicate the sterilization process and wire actuation limits the force application capability since the wires can apply only pulling forces (i.e.,buckle when pushed). SMA suffers from hysteresis and low operation frequency due to the time necessary for temperature changes to affect its martensite/austenite change. Also, the various designs of catheters do not meet the force application capabilities required for surgical tool manipulation.

Other approaches have been reported describing snake robots using a flexible backbone for snake-like robots (e.g., see I. Gravagne and I. Walker, "On the Kinematics of Remotely-Actuated Continuum Robots," IEEE International Conference on Robotics and Automation, pp. 2544-2550, 2000; I. Gravagne and I. Walker, "Kinematic Transformations for Remotely-Actuated Planar Continuum Robots," IEEE International Conference on Robotics and Automation, pp. 19-26, 2000; C. Li and C. Rhan, "Design of Continuous Backbone, Cable-Driven Robots," *ASME Journal of Mechanical Design*, vol. 124, pp. 265-271, 2002; G. Robinson and J. Davies, "Continuum Robots—a State of the Art," IEEE International Conference on Robotics and Automation, pp. 2849-2853, 1999). These efforts, however, focused on large scale snake-like robots that used one flexible backbone actuated by wires (see S. Hirose, *Biologically Inspired Robots, Snake-Like Locomotors and Manipulators*: Oxford University Press, 1993). Also, these designs have a number of limitations including that wire actuation in only a pull mode does not allow for large force actuation once the diameter of the snake is downsized to diameters less than 5 mm Further, when the diameter of the snake like unit is downsized, the stiffness of the snake-like unit is relatively low because it relies only on one central backbone supported by wires. This is strongly seen in the tensional stiffness.

Alternative designs of a 3 DoF wrist for MIS suturing were analyzed and a method was proposed to determine the workspace and to optimize the position of the entry port in the patient's body to provide optimal dexterity [M. Cavusoglu, I. Villanueva, and F. Tendick, "Workspace Analysis of Robotics Manipulators for a Teleoperated Suturing Task," IEEE/RSJ International Conference on Intelligent Robots and Systems, Maui, HI, 2001]. Also, three architectures of endoscopic wrists: a simple wire actuated joint, a multi-revolute joint wrist, a tendon snake-like wrist; have been analyzed and these joints compared in terms of dexterity and showed the superiority of the snake-like wrist over the other two wrists in terms of dexterity [A. Faraz and S. Payandeh, "Synthesis and Workspace Study of Endoscopic Extenders with Flexible Stem," Simon Fraser University, Canada 2003].

In chest and abdomen minimally invasive surgery, the entry portals for surgical instruments are usually placed some distance apart, and the instruments approach the operative site from somewhat differing directions. This arrangement makes it possible (though sometimes inconvenient and limiting) for telesurgical systems, such as the DaVinci or Zeus, to use rather large robotic slave manipulators for extracorporeal instrument positioning. The optimal placement of entry portals based on dexterity requirements for particular procedures is an important subject and has recently been addressed by several authors [L. Adhami and E. C. Maniere, "Optimal Planning for Minimally Invasive Surgical Robots," *IEEE Transactions on Robotics and Automation*, vol. 19, pp. 854-863, 2003; J. W. Cannon, J. A. Stoll, S. D. Sehla, P. E. Dupont, R. D. Howe, and D. F. Torchina, "Port Placement Planning in Robot-Assisted Coronary Artery Bypass," *IEEE transactions on Robotics and Automation*, vol. 19, pp. 912-917, 2003]. In contrast, with minimally invasive surgery of the throat, the size and location of the entry port is pre-determined and no such optimization is possible.

The upper airway of the throat is a long, narrow, and irregularly shaped organ that includes the pharynx (throat), hypopharynx, and larynx, commonly referred to as the voice box. These areas are subject to a variety of benign and malignant growths, paralysis, and scar tissue formation requiring surgical interventions for excision and/or reconstruction. These procedures also often must be performed past the vocal cords closer to the lungs. In order to maintain the voice characteristics, it is very important to be able to reconstruct the vocal cord region as accurately as possible. These procedures (e.g., partial or total laryngectomy, vocal fold repositioning, and laryngotracheal reconstruction) are routinely performed using open surgical techniques at the expense of damaging the integrity of the framework supporting the laryngeal cartilage, muscle, and the connective tissue vital to normal function. A minimally invasive endoscopic procedure is generally preferred over the open procedure, as it would preserve the laryngeal framework integrity, promote faster recovery and frequently overcome the need for tracheostomy.

There is shown in FIGS. 1A, B a conventional minimally invasive system that is used for the performance of laryngeal surgery. As illustrated, the internal regions of the airway are accessed through the use of an array of long instruments (usually ranging between 240 to 350 mm long) through a laryngoscope that is inserted into the patient's mouth and serves as a visualization tool and a guide for surgical instrumentation. The laryngoscope is typically 180 mm long with an oval cross-section usually ranging between 16-20 mm in width at its smallest cross section.

This surgical setup involves the surgeon manipulating several long tools, instruments or devices (for example, one tool for suction and another for tissue manipulation). The conventional instruments or devices, as indicated herein, are constrained by design to provided four (4) degrees of freedom of motion (or less) and also are characterized as lacking tool-tip dexterity. Consequently, such instruments or devices do not provide the surgeon with the required tip dexterity to allow the user to perform delicate and accurate surgical procedures such as for example, soft tissue reconstruction and sewing. Further, the vocal folds preclude the performance of surgical procedures past them using such instruments or devices.

Consequently, and due to these limitations, laryngeal minimally invasive surgery is currently limited to simple operations such as microflap elevation, excisional biopsies, and removal of papilloma using laser or powered microdebrider.

Functional reconstructive procedures (e.g., tissue flap rotation or suturing), are not performed in throat minimally invasive surgery, although, reconstruction of the vocal fold structures as accurately as possible is crucial for maintaining the voice characteristics. Suture closure of surgical defects has been shown to reduce scar tissue, shorten healing time, and result in improved laryngeal function and sound production (D. J. Fleming, S. McGuff, and C. B. Simpson, "Comparison of Microflap Healing Outcomes with Traditional and Microsuturing Techniques: Initial Results in a Canine Model," *Ann Otol Rhinol Laryngol.*, vol. 110, pp. 707-712, 2001; P. Woo, J. Casper, B. Griffin, R. Colton, and C. Brewer, "Endoscopic Microsuture Repair of Vocal Fold Defects," *J. Voice*, vol. 9, pp. 332-339, 1995). This seemingly simple operation is very difficult, if not impossible, to perform in laryngeal minimally invasive surgery.

Although laryngeal surgery is exemplary, many other minimally-invasive surgical procedures have similar needs for precise, high dexterity motions in confined spaces within a patient's body. Further, it is often necessary to operate multiple instruments in close proximity to each other, where the instruments are inserted into the body through roughly parallel access paths in confined spaces such as the throat. Further, the physical size of the instruments is often a significant factor in determining the feasibility of procedures. Further, as instruments are constructed to be smaller-and-smaller, designs using conventional approaches involving complicated linkages become more and more difficult and costly to fabricate and are increasingly susceptible to limitations due to backlash and other factors.

It thus would be desirable to provide improved methods and devices for minimally invasive surgeries. It also would be desirable to provide new devices and systems particular suited and adaptable for use with a wide range of minimally invasive surgical techniques that provide a similar freedom of motion at the treatment site as would be experienced using open surgical procedures or techniques. It also would be desirable to provided such minimally invasive devices and systems that provide such motion in a constrained surgical environment such as that presented in the throat and sinus. It also would be desirable to provide methods for treating any of a number of organs or areas of a body, more specifically the throat and sinus, using such devices and systems. It would be desirable to provide methods and devices that are capable of performing surgery on particularly challenging sites such as the throat. It would be highly desirable to provide methods and devices that are configurable to operate at multiple physical scales, ranging from small to extremely small, without requiring fundamental changes in the design concept approach. Such methods and devices should overcome the deficiencies of the presently available methods and devices.

SUMMARY OF THE INVENTION

The present invention features systems, devices and apparatuses for use in the performance of any of a number of minimally invasive surgical, diagnostic or therapeutic methods and/or techniques. In more particular embodiments, such systems, devices and apparatuses are particular adaptable and suitable for use in the performance of any of a number of minimally invasive surgical, diagnostic or therapeutic methods and/or techniques in confined areas such as a mammalian throat. Also featured are minimally invasive surgical, diagnostic and/or therapeutic methods that embody or use such systems, devices and apparatuses.

In particular embodiments, the present invention features a distal dexterity apparatus including one or more distal dexterity devices. In exemplary embodiments, each of the one or more distal dexterity devices comprises minimally invasive surgery tools and is configured and arranged with end-tip dexterity for enhanced manipulation. In particular, the distal dexterity apparatus comprises at least one, preferably a plurality, most preferably three distal dexterity devices that comprise in more specific embodiments robotic arms. A portion of each of the distal dexterity devices is snake like and the snake like portion is re-configurable (i.e., capable of being bent) in any of a number of fashions so as to in effect maneuver the surgical instrument/device and put it in a desired position with respect to the surgical site.

In further embodiments, the snake like portion is a multi-backbone snake-like mechanism. In particular embodiments, the snake-like portion comprises a system of a plurality or more of flexible backbones, more specifically a system comprising a centrally located backbone and a plurality or more of, more specifically three or more, secondary backbones that are spaced from and about the centrally located backbone. Such a flexible backbone system according to the present invention advantageously achieves high structural stiffness in bending and torsion, particularly when compared to that achievable with conventional systems that embody wires. Further, such a flexible backbone system according to the present invention advantageously eliminates small precision joints as required with conventional systems that embody articulated joints, thereby reducing manufacturing costs and avoiding designs issues associated with backlash. In more particular embodiments, the flexible backbones are flexible tubular members and more specifically the tubular members comprising the secondary backbones are about the same as, essentially the same as, or is the same as the tubular member comprising the centrally located backbone.

Another portion of the distal dexterity device comprises the surgical instrument/device so as to provide the distal dexterity device with the capability of performing surgical actions such as sewing, gripping, soft tissue manipulation, cutting and suction of saliva, blood and other materials from the surgical site. In further embodiments, the distal dexterity device includes a modular detachable or fixed tip element or wrist unit that provide the capability of performing the functions such as, for example, needle holding, tissue removal and suction capabilities needed for various surgeries. In a specific embodiment, the distal dexterity device includes a detachable or fixed cutting mechanism. In further specific embodiments, the wrist unit is removably mounted to the snake like portion, for example, by mating threaded portions, by providing a frictional fit between the snake like portion and the wrist unit, or by any other known types of removable attachment. This advantageously yields a distal dexterity device that can be modified as desired, particularly during the conduct of the procedure or technique, so as to provide the surgical function(s) required in a given procedure. Thus, a single unit can be interchangeable for a variety of different types of surgical functions by simply changing the writs units removable secured to the snake like portion.

In further embodiments, the wrist unit is moveably coupled to the snake-like portion so as to allow the wrist unit to be separately moved with respect to the snake-like portion, thereby allowing finer manipulation of the surgical instrument with respect to the treatment site. More particularly, the mechanism that moveable couples the wrist unit and the snake-like unit is configured and arranged so as to provide the wrist unit with one (1) or more degrees of freedom of motion, more specifically three (3) or more degrees of freedom of motion, with respect to the snake-like unit. In specific embodiments, one of the one or more degrees of freedom includes moving the wrist unit axially (e.g., away from or towards the snake-like portion). Consequently, such a distal dexterity device provides three (3) to five (5) degrees of freedom of motion (i.e., 2 degrees of freedom for the snake-like portion and 1-3 degrees of freedom associated with the moveable coupling mechanism).

In further embodiments, the moveable coupling mechanism and the wrist unit are configured and arranged so that the wrist unit is removably operably coupled to the moveable coupling mechanism. In this way, and as further described herein, the surgeon can decouple one wrist unit and attach another wrist unit having for example a different tool without requiring removal of the distal dexterity apparatus from the patient. In yet further embodiment, the moveable coupling mechanism is further configured and arranged so as to act as a clamping mechanism whereby the wrist unit is put into mechanical engagement (e.g., frictional engagement) with the a portion of the snake-like unit.

In further embodiments, the distal dexterity apparatus includes one or more device manipulation units, each being operable coupled to one of the one or more distal dexterity devices. In more particular embodiments, each device manipulating unit is configured and arranged so as to control the position of a long axis of the associated distal dexterity device with respect to a base member. In preferred embodiments, each device manipulating unit is configured and arranged so the distal dexterity device, including the portion containing the wrist unit, is capable of exhibiting one (1) or more degrees of freedom, more particularly a plurality or more of degrees of freedom and more specifically four (4) degrees of freedom and so as to control one or more of the angle of approach, the rotation about and the position along the long axis of the distal dexterity device about an axis of rotation.

In further embodiments, each distal dexterity device includes an actuation unit that is operably coupled to the snake-like portion and is configured and arranged so as to cause the snake-like portion to re-configure (e.g., bend) and thereby orient the surgical instrument/wrist unit so as to be in a desired orientation and location with respect to the treatment site. In the case where the snake-like portion comprises a flexible backbone system as described herein, the actuation unit is configured and arranged so as to act on one or more of the flexible backbones of the flexible backbone system thereby causing such reconfiguration. In particular embodiments, when the flexible backbone system comprises a centrally located backbone and a plurality or more of secondary backbones, the actuation unit is configured and arranged to act on one or more of the secondary backbones so as to achieve such reconfiguration. It should be understood that such acting on the secondary backbones by the actuation unit includes developing and applying one of a pushing or pulling force to respective secondary backbones. For example, a pulling force can be applied to one or more of the plurality or more of secondary backbones and a pushing force can be concurrently applied to another one or more of the plurality or more of secondary backbones.

In further particular embodiments, the actuation unit also is operably coupled to the moveable coupling mechanism that moveably couples the wrist unit to the snake-like portion, and is configured and arranged so as to cause the coupling mechanism to move the wrist unit in one or more directions with respect to the snake-like unit. In particular embodiments, the coupling mechanism comprises a plurality or more, more specifically three or more, separately moveable actuating members that are each operably coupled to the actuation mechanism and which move with respect to the snake-like portion (i.e., movement of members do not cause appreciable or movement by the snake-like portion).

The actuation mechanism is more particularly configured and arranged to move any one or more of the one or more actuating members in a predetermined fashion as to thereby cause the wrist unit to move with respect to the snake-like unit so as to thereby change the orientation and position of the surgical instrument with respect to the treatment site. In specific embodiments, the actuation mechanism in combination with the coupling mechanism can cause the wrist unit to be remotely actuated and moved so as to have one or more, more specifically in three or more degrees of freedom of motion. In more particular embodiments, the actuating members are cylindrical members, such as tubular members or solid cylindrical members such as wire. As also indicated herein, the actuation mechanism is configured and arranged so as to cause the actuating members to act in a fashion that puts the wrist unit into mechanical engagement with a portion of the snake-like portion.

In further embodiments, when the snake-like portion comprises a flexible backbone system including a plurality or more of tubular secondary backbones, the actuating members are arranged so as to extend within the lumen or passage of the secondary backbones from the coupling mechanism to the actuation unit.

Other aspects and embodiments of the invention are discussed below.

BRIEF DESCRIPTION OF THE DRAWING

For a fuller understanding of the nature and desired objects of the present invention, reference is made to the following detailed description taken in conjunction with the accompanying drawing figures wherein like reference character denote corresponding parts throughout the several views and wherein.

DEFINITIONS

Figure 1A:
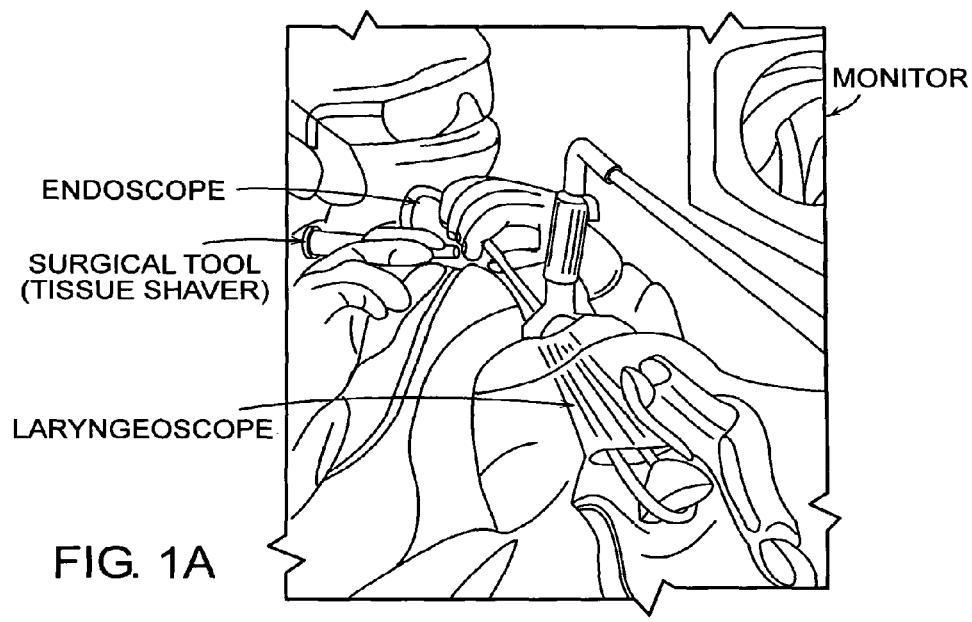
FIGS. 1A,B are various illustrations showing a conventional minimally invasive system that is used for the performance of laryngeal surgery.
Figure 1B:
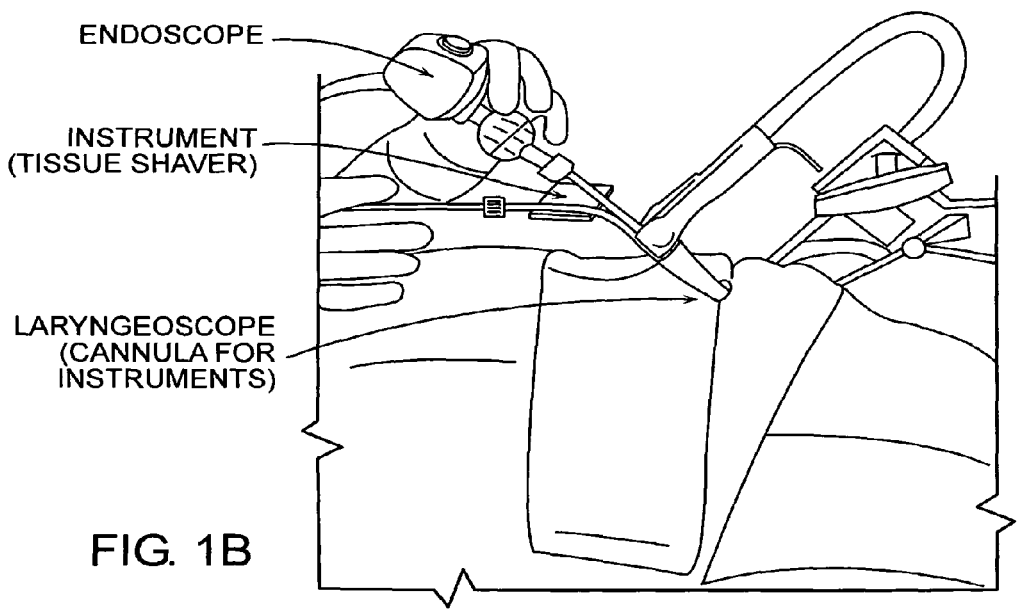

The instant invention is most clearly understood with reference to the following definitions:

As used in the specification and claims, the singular form "a", "an" and the include plural references unless the context clearly dictates otherwise.

As used herein, a "patient" is a vertebrate, preferably a mammal, more preferably a human. Mammals include, but are not limited to, murines, simians, humans, farm animals, sport animals, and pets.

DESCRIPTION OF THE PREFERRED EMBODIMENT

The present invention provides improved methods, systems and devices/surgical instruments for performing minimally invasive techniques including surgery, surgical procedures, treatment and/or diagnostic procedures. In particular, the present systems and devices are suitable for performing minimally invasive techniques whereby the operable end provided is capable of moving with degrees of freedom comparable to that seen when using open surgery techniques. In addition, systems, methods and devices of the present invention are particularly suitable for performing minimally invasive techniques/procedures under what might be considered challenging conditions for conventional minimally invasive techniques. For example, some surgeries are more challenging than others due to the shape of the surgical site and/or the presence of other tissue proximal the surgical site that makes access to, and manipulation at, that site difficult. Still further, the route or path taken to gain access to the surgical site can be lengthy and/or present a complex/tortuous path that also would make accessing the site and/or manipulation at that site difficult. In the later case for example, minimally invasive surgeries of the upper airway, including the throat and larynx, typically present challenges when using conventional instruments/devices, systems and methods because of the shape of the airway and position of the larynx, the need to perform complex procedures on or beyond the vocal folds, and the need to simultaneously manipulate 2-3 long instruments through a predetermined entry port that is limited by the size and shape of the throat.

The present invention and preferred embodiments thereof, are particularly suitable for performing minimally invasive throat surgeries, as such the following discussion describes the methods, systems and devices of the present invention with particular reference to devices, systems and methods for performing minimally invasive throat surgeries. This shall not be construed as limiting the devices, systems and methods of the present invention to the these embodiments, however, as it is contemplated and thus within the scope of the present invention to adapt the devices, systems and methods described herein so as to be used in any of a number of minimally invasive surgeries and procedures, including, but not limited to, general micro-surgery, brain surgery, ear, nose and throat (ENT) surgery, sinus surgery, other head-and-neck surgery, spinal surgery, micro-vascular surgery, drug delivery, and surgeries on bones (e.g., removal of osteolytic lesions in the bones, boring bones, etc.). As such, it is contemplated that the specific design parameters or other characteristics set forth hereinafter in relation to throat surgeries shall be modified as required so as to provide the appropriate dimensions and geometries as required to perform such other minimally invasive surgeries/techniques. For example, the length of the distal dexterity device holder as herein described, is adapted to suit the particular conditions for a given procedure.

Figure 2:
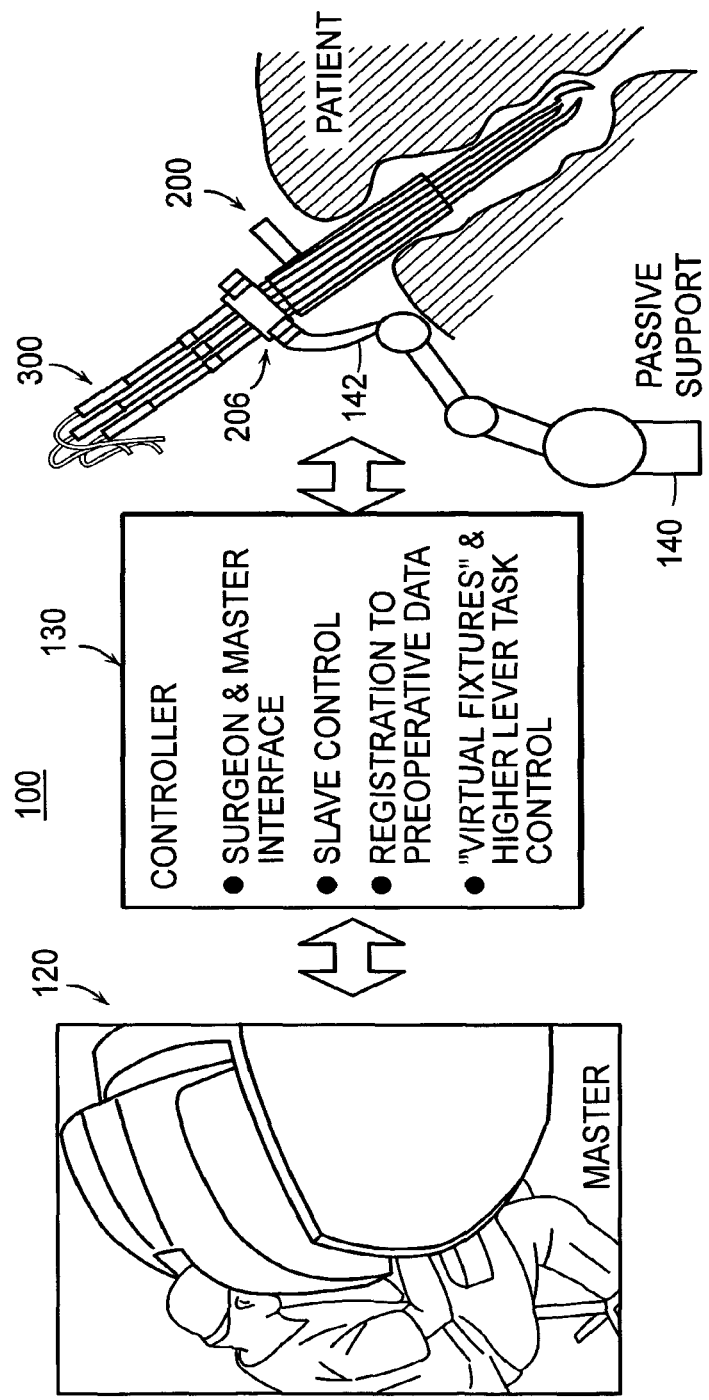
FIG. 2 is a schematic view illustrating a minimally invasive system according to the present invention for the performance of a laryngeal surgical procedure.

Referring now to the various figures of the drawings wherein like reference characters refer to like parts, there is shown in FIG. 2 a schematic view of an exemplary illustrative minimally invasive system 100 according to the present invention, particularly configured for the performance of a laryngeal surgical procedure. Such a minimally invasive system 100 of the present invention is easily adapted for use with other apparatus and devices as is known in the art so as to yield a telesurgical robotic architecture or arrangement including, but not limited to the same master-slave architecture as known architectures (e.g., the DaVinci® telescopic robot (G. Guthart and K. Salisbury, "The Intuitive™ Telesurgery System: Overview and Application," IEEE International Conference on Robotics and Automation, pp. 618-621, 2000)). Although the illustrated minimally invasive system 100 is particularly configured for throat surgery, the system and components thereof are adaptable for other minimally invasive microsurgery applications, more specifically applications performed in confined spaces. In the illustrated exemplary embodiment, the minimally invasive system 100 includes a master interface 120, a controller 130, a support 140 and a distal dexterity apparatus 200 according to the present invention that is described further herein.

The master interface 120 is any of a number of devices known in the art, including that referred to hereinabove, that provides visual and force feedback to the surgeon performing the procedure as well as providing a mechanism by which the surgeon can remotely actuate and manipulate the instruments and other devices of the distal dexterity apparatus 200. The controller 130 is operably coupled to the master interface 120 and the distal dexterity apparatus 200 so as to further provide master-slave integration and also to control the operation of the distal dexterity apparatus 200 as herein described.

The support 140 is any of a number of mechanisms, devices or apparatuses known to those in the art, both active and passive, whereby the distal dexterity apparatus 200 can be appropriately and correctly positioned by the surgeon or other medical personnel with respect to a natural (e.g., mouth) or man-made opening in the body of a patient for performance of the surgical, diagnostic and/or therapeutic procedure or technique as well as to hold the distal dexterity apparatus in essentially fixed relation at least through the time of the surgical/therapeutic procedure/technique requiring the use of the distal dexterity apparatus. In the illustrated embodiment, the support 140 is a passive support, that is a support that is configured and arranged so the surgeon can move the distal dexterity apparatus 200 to the appropriate position with respect to the opening and which will keep the distal dexterity apparatus in fixed relation. In more specific embodiments, such a passive support includes locking mechanisms as are known to those skilled in the art that, when actuated, preclude further movement in the locked direction.

It also is contemplated and within the scope of the present invention for the support 140 to be an active or robotic support whereby the distal dexterity apparatus 200 is manipulated by the support via the controller 130 or other controlling mechanism (e.g., controller with an application program for execution therein), as are known to those skilled in the art. In this way, the distal dexterity apparatus 200 is moved by the support 140 from a stored or pre-surgical position to a position proximal the entry site or the opening (natural or man made). Thereafter, the support 140, for example under control of the surgeon, would further manipulate the distal dexterity apparatus 200 so that the operable end 304 of the apparatus is inserted into the opening and positioned proximal the treatment site within the body of the patient.

In further embodiments, and as described in further detail herein, the distal dexterity apparatus 200 is configured and arranged so as to include at least one distal surgical instrument or device, more preferably a plurality of distal surgical instruments or devices, more particularly three or more such distal surgical instruments or devices. The number of distal surgical instruments/devices that the distal dexterity apparatus 200 is configured with is based on the particular needs of the procedure/technique to be performed and any limitations imposed by the size and configuration of the pathway in the body through which the operable end of the distal dexterity apparatus 200 travels to reach the treatment site from the opening.

The controller 130 also is configured and arranged so as to control the operation and movement of the each of the surgical instruments/devices of the distal dexterity apparatus 200. More particularly, the controller 130 is configured and arranged so as to control each distal dexterity device assembly 300 (hereinafter distal dexterity device) of the distal dexterity apparatus 200 including the surgical instrument or device that is associated with a given distal dexterity device. In this way, and as with the telesurgical environment referred to above, the surgeon can remotely manipulate the surgical instrument or device based on the force and visual feedback information presented by the master interface 120 as well as manipulating the distal dexterity device associated with a given surgical instrument or device so the surgical instrument or device at the operable end 304 of the distal dexterity device is appropriately positioned with respect to the treatment site (e.g., location and orientation) and so that the surgical instrument can perform or carry out the procedure (e.g., suturing tissue, cutting and grabbing a tissue biopsy, suctioning fluid).

In further embodiments, the distal dexterity apparatus 200 is configured and arranged so that each distal dexterity device 300 can be easily removed from the distal dexterity apparatus and/or insertion of another distal dexterity device therein without first requiring the removal of the distal dexterity apparatus from within the bodily opening to perform such tasks. As indicated above, the specific size and configuration of the bodily opening may impose a limit on the number of distal dexterity devices 300 that can be inserted into the opening. This re-configurable feature of the distal dexterity apparatus 200 provides a mechanism by which, a surgeon or other surgical personnel can easily reconfigure the distal dexterity apparatus, including the one or more surgical instruments/ devices being provided, in accordance with the needs of the procedure.

Figure 3:
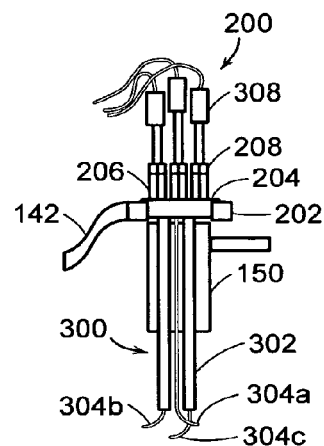
FIG. 3 is a side view of the distal dexterity apparatus of FIG. 2.

The distal dexterity apparatus 200 illustrated in FIGS. 2-3, presents a three-armed robot that works through a laryngoscope 150. This shall not be construed as a limitation as it is contemplated that the distal dexterity apparatus be adapted for use with other devices known to those skilled in the medical arts (e.g., endoscope, laparoscope) that have a similar function of providing a cannula or lumen like member through which the distal dexterity apparatus 200 of the present invention can work and access the treatment site.

In the illustrated embodiment, the distal dexterity apparatus 200 is configured and arranged with a visualizing apparatus or device as is known to those skilled in the art, whereby the surgeon is presented with a visual image of the treatment site and the operable end(s) 304 of the distal dexterity device(s) 300 disposed within the body of the patient and proximal the treatment site. Also, in the illustrated embodiment, the operable ends 304b,c of two distal dexterity devices 300 are configured and arranged so as to include any one of a number of surgical instruments/devices that can be used for manipulation of tissue (e.g., scalpels, forceps, etc.) and the operable end 304a of the other distal dexterity device is configured with an instrument or device for suctioning tissue, bone, cartilage, fluids and the like from the treatment site. In the within discussion, if reference is being made to the operable ends of the distal dexterity device 300 in general then the reference numeral 304 is used; when referring to one or more specific operable ends the reference numeral further includes an alpha character.

It also is contemplated that a distal dexterity device 300 including the operable end 304 thereof, be configured and arranged so as to be capable of delivering a therapeutic medium to the treatment site. For example, the operable end 304 can be configured so as to include an injection device including the therapeutic medium or be configured with a needle like element that is fluidly coupled to a source of the therapeutic medium for example a reservoir located within the distal dexterity device. The surgeon or other medical personnel would thus remotely position the operable end of the injection device or needle element within the tissues of the treatment site or other appropriate location and then cause the therapeutic medium to be delivered from the injection device/ reservoir to the tissues.

In particular embodiments, the distal dexterity apparatus 200 includes a base 202, a rotating base member 204, one or more device manipulation units 206 and one or more distal dexterity devices 300. The base 202 is operable coupled to an arm 142 of the support 140 and also is configured and arranged to rotatably, moveably receive therein the rotating base member 204. The rotating base member 204 and the base 202 are respectively configured and arranged using any of a number of techniques and/or devices known to those skilled in the art, whereby the rotating base member is rotated within the base about a first axis of rotation.

The one or more device manipulation units 206, preferably a plurality or more of the manipulating units, is mounted using any of a number of techniques known to those skilled in the art to the rotating base member 204. Each of the device manipulating devices 206 is configured and arranged, as herein more particularly described, so as to hold each of the distal dexterity devices 300. In more particular embodiments, each device manipulating unit 206 is configured and arranged so as to control the position of a long axis of the associated distal dexterity device 300 with respect to the rotating base member 204. In preferred embodiments, each device manipulating unit 206 is configured and arranged so the distal dexterity device 300, including the operable end 304 thereof, is capable of exhibiting one (1) or more degrees of freedom, more particularly a plurality or more of degrees of freedom and more specifically four (4) degrees of freedom and so as to control one or more of the angle of approach, the rotation about and the position along the long axis of the distal dexterity device about a second axis of rotation.

As each of the distal dexterity device 300 is operable coupled to the rotating member 204 by the associated device manipulating unit 206; when the rotating base member 204 is rotated about the first axis of rotation, the operable ends 304 of each distal dexterity device 300 also are rotated about the first axis of rotation. In this way, a surgeon can rotate the operable ends 304 of the respective distal dexterity devices 300 of the distal dexterity apparatus 200 so the operable end of the surgical instrument/ device next to be used is appropriately positioned with respect to the treatment site (i.e., can select and position the surgical instrument/ device next to be used). This also has the beneficial effect of minimizing the potential for, if not avoid, collisions between operable ends 304a-c as an operable end is further manipulated as herein described in connection with the use of the surgical instrument/ device associated with the particular distal dexterity device.

Figure 4A:
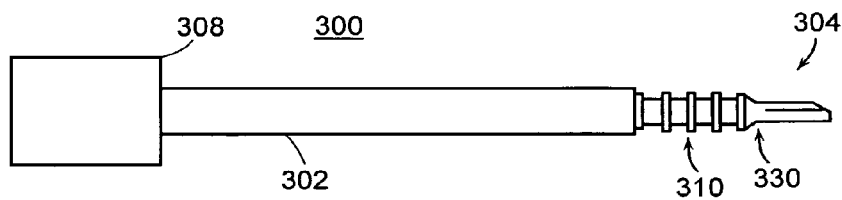
FIG. 4A is a schematic view of a distal dexterity device of FIG. 2.
Figure 4B:
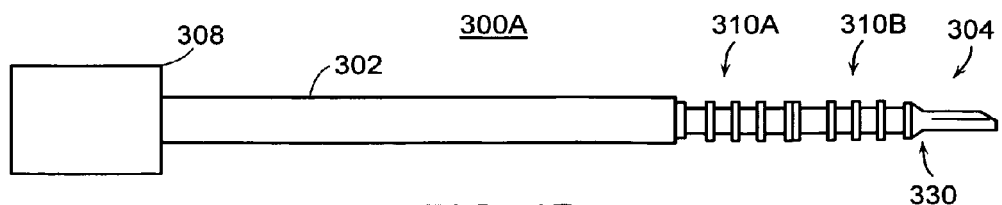
FIG. 4B is a schematic view of another distal dexterity device with stacked manipulation devices.
Figure 5:
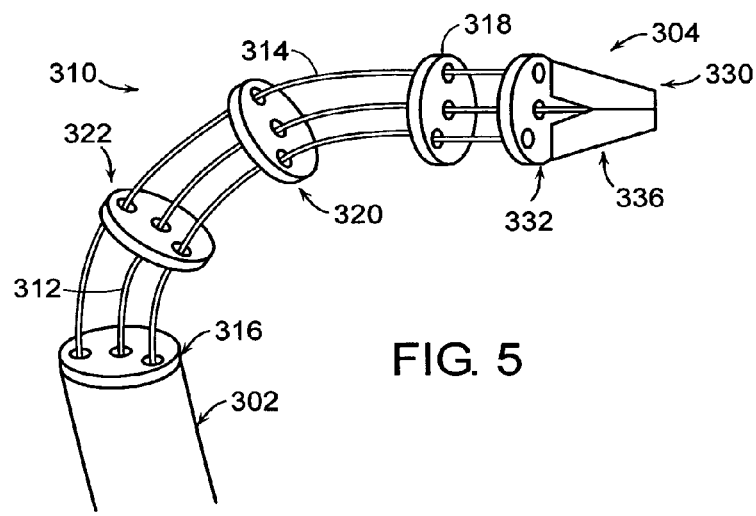
FIG. 5 is a perspective view of an end portion of the distal dexterity device of FIG. 4A.
Figure 6:
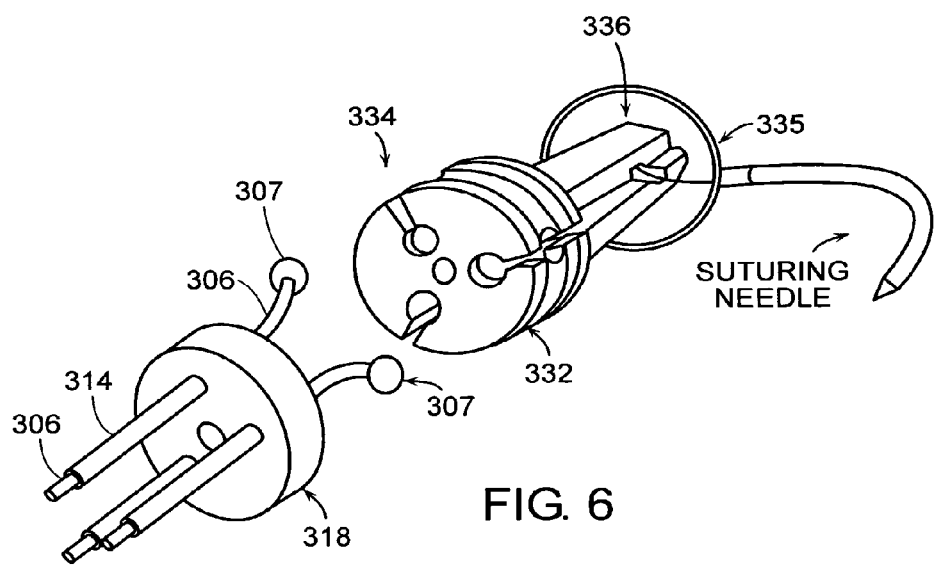
FIG. 6 is an exploded perspective view of a portion of FIG. 5.

Now with reference also to FIGS. 4-6, each distal dexterity device 300 includes a holder member 302, the operable end 304, an actuation unit 308, wires 306 and wire ends 307. The operable end 304 also is configured and arranged so as to include a manipulation device 310 and, in more specific embodiments, a tip member or wrist device 330. The distal dexterity devices of the present invention provide the necessary flexibility for bypassing obstacles as the operable end 304 is traversing the pathway to the surgical site. In more particular embodiments, the distal dexterity devices 300 of the present invention are capable of delivering torque about the backbone structure of the manipulating device 310 thereby transforming the rotation of the manipulating device about its axis into rotation, which is a valuable property for suturing and tissue manipulation in a confined space.

The manipulation device 310 and the actuation unit 308 are operable coupled to respective ends of the holder member 302. In particular embodiments, the holder member 302 is a tubular member (e.g., thin tube) of a biocompatible material characterized as having sufficient strength to withstand the loads imposed during a procedure/technique as the holder member is being rotated or moved axial by the manipulation unit 206 and when the actuation device 308 is acting on the manipulation device 310 for re-configuring (e.g., bending) the manipulation device. The lumen within the holder member 302 also establishes a pathway through which the secondary back bones 314 along with any internal wires 306 run between the manipulating device 310 and the actuation device 308. This preferably also creates a barrier between the axially moving elements of the distal dexterity device and the surrounding tissues. The width and length of the holder member 302 is set based on the particulars of the procedure to be performed. For example, in throat surgical procedures it is desirous for the operable end 304 of the distal dexterity device to extend about 180-250 mm into the throat. Thus, the length of the holder member 302 would be set so as to accomplish this. Similarly, the width of the holder member 302 is set based on the size of the opening, the size of the passage, the area available at the surgical site and the interior dimensions of the member that is typically inserted into the opening (e.g., laryngoscope).

The holder member 302 is in the form of a rigid tubular element, a flexible tubular element or device or is composed or rigid tubular portions and flexible tubular portions to fit the use and function of the distal dexterity apparatus 200. For example, the portion of the holder member 302 that is disposed with the device manipulation unit 206 may be a rigid member and other portions of the holder member may be flexible in construction. The flexible portions of the holder member 302 can comprise for example, a flexible device such as a catheter, flexible endoscope, or another snake-like unit. In another example, the external portion of the holder member 302 (i.e., portion beyond the external to the device manipulation device 206) would comprise a flexible portion and the remainder of the holder portion including the portion within the patient would comprises a rigid portion.

Also, when the secondary backbones 314 pass through a flexible portion of the holder member 302, the secondary backbones are preferably constructed or selected from materials and structures that are flexible in bending for those portions that remain inside the holder member 302 but still stiff in the axial direction for transmission of force in either a push or pull direction. In further embodiments, the secondary backbones 314 are supported in flexible sheaths so as to further prevent buckling in a long flexible section. Such a structure advantageously yields a system of the present invention that is useable in flexible endoscopy applications and also in intracavitary procedures such as ablations inside the heart. Such a design also advantageously allows multiple snake-like units to be placed sequentially in order to further increase dexterity, as discussed further herein.

As shown more clearly in FIG. 5, the manipulation device 310 includes a base disk or member 316, an end disk or member 318, intermediate spacer disks or members 320, a central backbone 312, and secondary backbones 314. The foregoing are arranged and configured so as to yield a snake-like unit that is generally categorizable as a continuous non-extensible multi-backbone unit.

The central and secondary backbones 312, 314 are generally in the form of a flexible tubular member, such as a super-elastic tube, more specifically a tube made from NiTi. More generally, the secondary backbones 314, are constructed or selected from materials and structures (e.g., diameter and wall thickness) so that they are flexible in bending but still stiff in the axial direction for transmission of force in either a push or pull direction and the central backbone are constructed or selected from materials and structures (e.g., diameter and wall thickness) so it flexible in bending. Also, such materials and structures preferably yield a member that does not do not permanently deform (e.g., buckle) when the manipulation device 310 is being manipulated or bent.

In exemplary embodiments, there are three secondary backbones 314 arranged about and spaced from the central backbone. It should be recognized that the number of secondary backbones 314 is set so as to provide the required bending motion while generally assuring that the central and secondary backbones 312, 314 do not permanently deform (e.g., buckle) when the manipulation device 310 is being manipulated or bent. The central tube or backbone 312 is the primary backbone while the remaining three tubes are the secondary backbones 314. In illustrative exemplary embodiments, the secondary backbones 314 are spaced equidistant from the central backbone 312 and from one another.

The central backbone 312 is attached or secured to the base member 316 and the end member 318 as well as to all of the intermediate spacer members 320. The secondary backbones 314 are attached to the end member 318 and are slidably disposed within apertures 322 provided in each of the base member 316 and the intermediate spacer members 320. In this way, the secondary backbones 314 are free to slide and bend through the apertures 322 in the base member 316 and intermediate spacer members 320. As herein described, the secondary backbones 314 are used for actuating the manipulating device 310 using one or a combination of both push and pull modes and also pass through the lumen or guiding channel(s) in the holder member 302.

The intermediate spacer members 320 are configured and arranged (e.g., spaced from one another) to prevent buckling of the central and secondary backbones 312, 314 and to maintain an equal distance between the secondary backbones and the central backbone. In further embodiments, the intermediate spacer members 320 are placed close enough to each other so that the shapes of the primary and secondary backbones 312, 314 are constrained to lie in a prescribed fixed distance apart. The intermediate spacer members are also arranged and fixed on the central backbone 312 such that they do not prevent the central backbone from bending while providing negligible friction to movement of the secondary backbones 314.

In preferred embodiments, the secondary backbones 314 are sized so as to have the same size as the primary backbone and therefore their bending properties are significant (i.e they can not be treated as wires). This allows the manipulation device 310 to be constructed so as to have a small diameter for use in confined spaces such as the throat while maintaining structural rigidity and simplicity of actuation. Also, by using push-pull elements for the actuation of the manipulation device 310, it is possible to satisfy the statics of the structure while preventing buckling of the backbones. This also allows the diameter of the manipulation device 310 to be reduced such as for medical applications requiring a diameter smaller than 4 mm.

The above described structure yields a snake-like device that embodies a flexible backbone system made up of a plurality or more of backbones 312, 314 that can advantageously achieve high structural stiffness in bending and torsion, particularly when compared to that achievable with conventional systems that embody wires. Further, such a flexible backbone system according to the present invention advantageously eliminates small precision joints as required with conventional systems that embody articulated joints, thereby reducing manufacturing costs and avoiding designs issues associated with backlash.

As herein described, the backbones 312, 314 also are configured and arranged so as to have more that one usage or function other than the above-described structural use (i.e., dual usage). The lumen or internal passage of the backbones 312, 314 are adaptable so as to be used to provide a pathway for passage of a fiber optic cable for example that can be used as a light source to illuminate the treatment site for visualization of the treatment site and the operable ends 304 of the distal dexterity devices 300.

The lumen or internal passage of one or more backbones are useable as a fluid passage for delivering fluids such as for delivery of a therapeutic medium or aspiration as well as for suctioning away fluid and/or debris. In such a case, it is contemplated that a given backbone 312, 314 and the distal dexterity device 300 would be adapted so as to be capable of performing these function(s). For example, the distal dexterity device 300 would be adapted so that the backbone internal passage would be fluidly coupled to an external source of fluid and/or suction source and the operable end 304 thereof would be adapted for delivery of the fluid and/or suction. Also for example, one secondary backbone 314 could be configured to fluid delivery while another backbone, such as the centrally located backbone 312, could be fluidly coupled to a suction source.

Additionally, the lumen or passage way of one or more backbones 312,314 are useable as a passageway in which passes the actuating members (i.e., wires 306) that comprise a mechanism to operably couple the wrist unit 330 and the manipulating device 310. The lumen or internal passages of one or more backbones 312, 314 of a first manipulating device 310*a* also are useable as a passageway for the secondary backbones 314 of a second manipulating device 310*b*.

In further embodiments, and with particular reference to FIG. 4B, the distal dexterity device 300*a* is configured and arranged so as to include two or more manipulating devices 310*a,b* that are stacked one upon the other. In such an application, the secondary backbones 314 for the second manipulation device 310*b* or second section would be passed through the secondary backbones of the first manipulation device 310*a* or first section. This allows for serial stacking of the second section on the first section and also creates a multisection snake that can be used for exploration and surgical intervention in deeper regions such as through the airways of the lung. Such stacking also necessarily allows each of the manipulation devices 310*a,b* to be actuated independent of each other. Thereby allowing the distal dexterity device to achieve or be capable of exhibiting two additional degrees of freedom for each manipulation device provided, while at the same time not being subjected to the limitations or concerns that are created with the addition of articulate joints in conventional systems.

In sum, an advantageous effect that flows from the architecture of the manipulation device 310 stems from the use of flexible backbones, thereby removing the dependency on small universal joints and wires as with conventional devices and systems. In addition to reducing manufacturing costs of the manipulation device as compared to conventional devices and this contributes to the possible reduction in size due to the small number of moving parts and the absence of standard miniature joints. Another advantage effect comes from the secondary use of tubes for the backbones, thus providing a secondary application for these backbones. As indicated herein these backbones can serve as suction channels, fluid channels, an actuation channel for the tool mounted on its distal end or as a source of light for imaging. In a particular embodiment, a mechanism (e.g., wire, tube) is passed through the central backbone 312 which mechanism is used to actuate or control the operation of the surgical tool/instrument/device associated with a given distal dexterity device 300.

In another embodiment of the present invention, the manipulation device 310 is configured and arranged so that one of the secondary backbones 314 is a redundant secondary backbone, which can be actuated to reduce the amount of force acting on the primary backbone and by doing so, reducing the risk of its buckling.

As indicated above, the operable end 304 includes a wrist unit 330 that is configured and arranged so as to provide or contain the surgical instrument/device/tool 336 for use during a given procedure. In the illustrated embodiment, the wrist unit 330 the surgical instrument/tool/device 336 is a gripper 336. In addition, to gripping tissue and as illustrated in FIG. 6, the surgeon can grip a suturing needle thereby allowing suturing of the tissue using the gripper. As indicated herein, in contrast to the present invention conventional minimally invasive instruments for throat surgical procedures have limited capabilities and suturing of tissue is one of the functions that are not possible with conventional instruments.

The manipulation device 310 of the present invention is capable of providing two degrees of freedom of motion for the distal tip of the tool, which degrees of freedom are associated with bending sideways in any direction. To further increase the capability or maneuverability of the surgical tool/instrument/ device 336, a coupling mechanism is provided moveable coupling the multi-parallel unit or wrist unit 330 and the manipulating device 310, which coupling mechanism is configured and arranged to provide an additional one (1) to three (3) degrees of freedom for delicate and accurate motions in a very confined space. Such a structure utilizes the architecture-inherent rigidity of parallel robots and supports further downsize scalability of the distal dexterity device, more particularly the manipulating unit 310, while maintaining useful structural rigidity.

The coupling mechanism comprises super-elastic actuation wires 306 having balls 307 attached to an end thereof and grooves or slotted apertures 334 provided in a moving platform 332 to which the tool 336 is affixed, which form spherical joints, and a flexible locking ring 335. The wrist unit 330 or milli-parallel unit as shown in FIGS. 5-6, uses the coupling mechanism, more specifically the super-elastic actuation wires 306 passing through the secondary backbones 314, spherical joints, and a moving platform 332 to which the tool 336 is affixed. The moving platform 332 is configured and arranged matching groves or slotted apertures 334 such that balls 307 attached to the end of the actuation wires 306 match its diameter. The flexible locking ring 335 is placed around the circumference of the moving platform to maintain these balls 307 inside their grooves 334.

Such a structure also yields a wrist unit 330 that is detachable from the manipulation device 310. For example, removing the flexible locking ring 335 and then removing the balls 307 from the grooves accomplish this detachment process. In this way, the moving platform 332 together with its tool 336 can be detached from the manipulation device 310.

In use and in exemplary embodiments, there are two operation modes of the coupling mechanism to use the detachable wrist unit 330 of the present invention. In the first mode of operation, the reconfiguring mode, the actuation wires 306 are extended outwards thereby allowing a new moving platform equipped with another tool to be attached. In this mode, the user would remove the locking ring 335, remove the balls from the moveable platform, insert the balls in another moveable platform and re-affix the locking ring. Once the tool and moving platform are attached then the actuation wires 306 are retrieved or withdrawn until the moving platform is secured on the end member 320 of the manipulation device 310.

In the other operating mode, which occurs during the performance or conduct of procedure/technique, the actuation wires 306 are used or manipulated in a predetermined manner to actuate namely move the moving platform 332 with respect to the manipulation device 206 as a three degree of freedom parallel platform with extensible links. The flexibility of the actuation wires 306 allows the motion of the moving platform 332 even though the actuation wires maintain perpendicularity to the end disk of the snake-like unit through their passage ports. In particular aspects the wires 306 can be extended to move the moveable platform 332 away from the manipulation device 206 basically in an axial direction as well as axially and in other directions. This operating mode allows the surgeon to further orient and position the tool, instrument or device affixed to the wrist unit 330 with respect to the treatment site.

Such moveably coupling of the wrist unit 330 to the snake-like manipulation device 310 allows the wrist unit to be separately moved with respect to the manipulation device, thereby allowing finer manipulation of the surgical instrument with respect to the treatment site. More particularly, the mechanism that moveably couples the wrist unit 300 and the manipulation device 310 is configured and arranged so as to provide the wrist unit with one (1) or more degrees of freedom of motion, more specifically three (3) or more degrees of freedom of motion, with respect to the manipulation device 310. Consequently, such a distal dexterity device 300 provides three (3) to five (5) degrees of freedom of motion (i.e., 2 degrees of freedom for the manipulation device 310 and 1-3 degrees of freedom associated with the moveable coupling mechanism described above).

Figure 7:
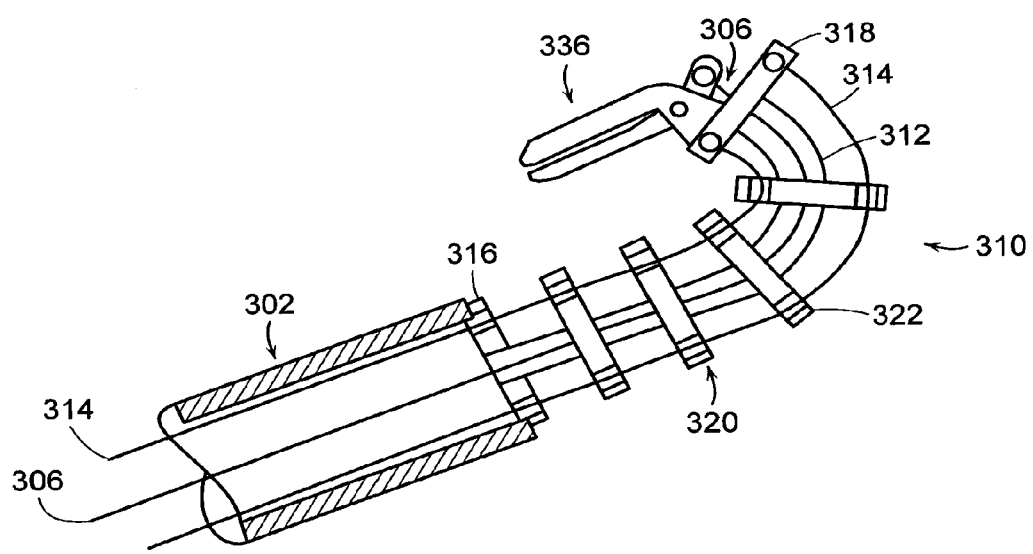
FIG. 7 is a perspective view of an end portion of an embodiment of the distal dexterity device of the present invention.

(¶) As shown in FIG. 7, the actuation wire 306 for the gripper/tool also is equipped with a fast connection to the gripper and is extended according to the kinematics of the distal dexterity device 300 to maintain the operation of the tool. This wire can also be used for micro-drill applications where it is also actuated in rotation.

Figure 8:
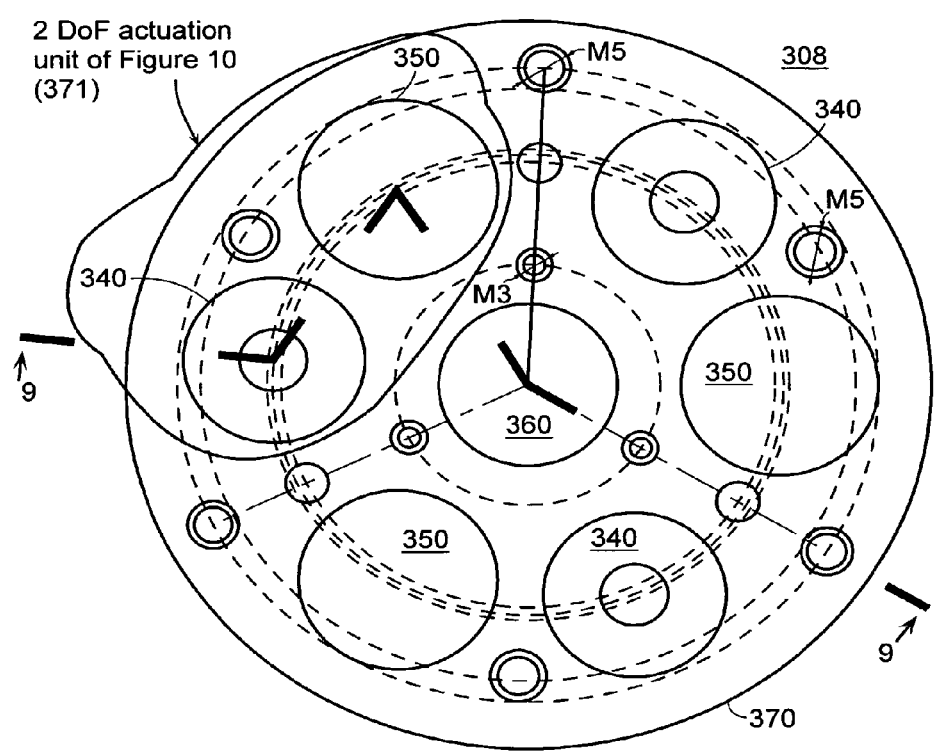
FIG. 8 is a top view of the base disk of the actuation unit of FIG. 4A.
Figure 9:
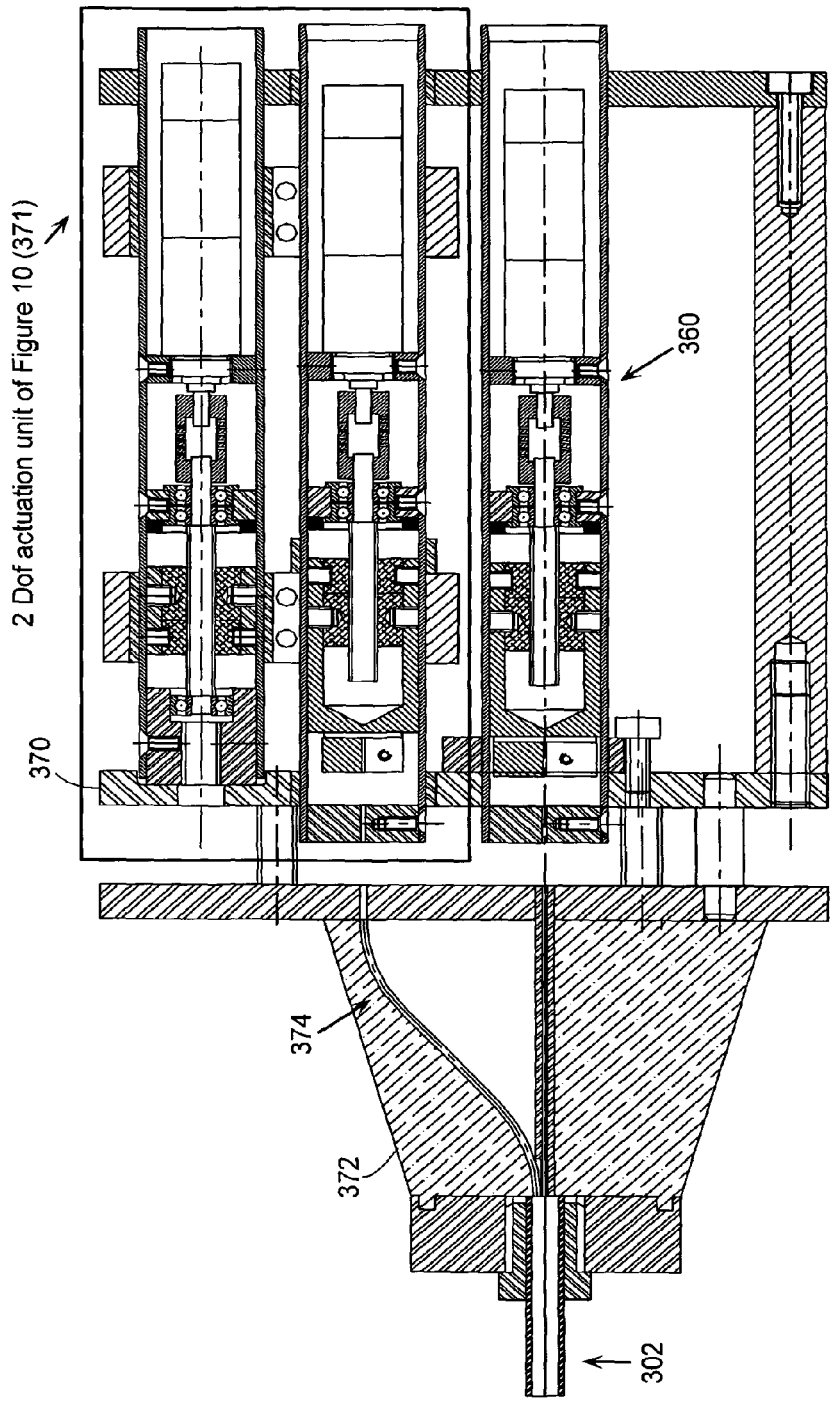
FIG. 9 is section view take along section line 9-9 of FIG. 8.
Figure 10:
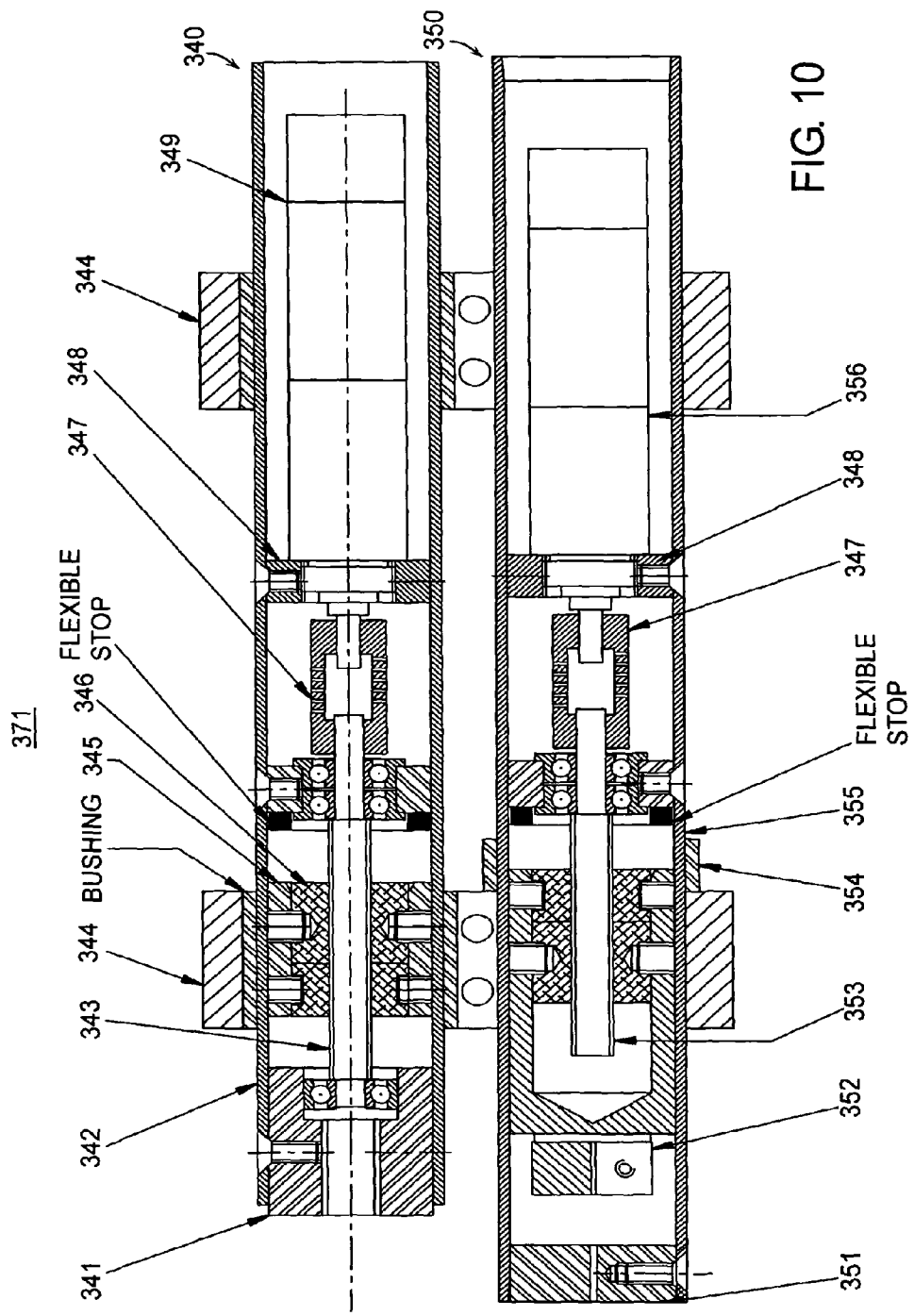
FIG. 10 is a side sectional view of one backbone actuation unit and one flexible wire actuation unit of FIG. 9.

Referring now also to FIGS. 8-9 there is shown various views of an exemplary actuation unit 308 according to embodiments of the present invention that manipulates the secondary backbones 314 and the actuation wires 306 operably coupled to the wrist unit 330 as well as the actuation wire 306 that can be used to actuate the surgical instrument/device. In exemplary embodiments, the illustrated manipulation device 310 according to the present invention includes three secondary backbones 314 and a central backbone. As such and as shown in FIG. 8, the actuation unit 308 comprises three pairs of a backbone actuation unit 340 and a wire actuation unit 350 and an actuation unit 360 for actuation of the surgical instrument, which are all mounted upon and to a base plate 370. In broad aspects, the actuation unit comprises N backbone actuation units 340 and N wire actuation units 350, where N is an integer greater than one, more particularly N is greater than or equal to two, and in a more specific exemplary embodiment N is three. In the case, where the tool is secured to the end member of the manipulation device 310 and there are no wires, then the actuation unit 308 is configurable so as to include only the backbone actuation units. The backbone actuation unit 340 and the wire actuation unit 350 are each three identical two degree of freedom linear actuators. The instrument actuation unit 360 is similar in construction and function to the wire actuation unit 350 and thus reference shall be made to the wire actuation unit for further details.

As more clearly shown in FIG. 9, the base plate 370 is coupled or secured to an interface member 372 that in turn is coupled or secured to an end of the holder member 302 of a given distal dexterity device 300. The interface member 372 is configured and arranged so as to include one or more guiding channels 374 for guiding each of the secondary backbones 314 exiting the holder member 302 to its respective backbone actuation unit 340 and correspondingly thus also guiding the corresponding actuation wires to its respective wire actuation unit 350.

The backbone actuation unit 340 includes a base connector 341, a main cylinder tube 342, a main lead screw 343, a slider bracket 344, a main piston 345, a lead screw nut 346, a flexible coupling 347, a gear motor base 348 and a main cylinder gear motor 349. The wire actuation unit 350 includes an external tube connector 351, a secondary piston 352, a secondary lead screw 353, a stopper ring 354, a secondary cylinder tube 355 and a secondary cylinder gear motor 356. The main cylinder 342 is attached rigidly to the base plate 370 and carries the secondary cylinder 355.

The secondary lead screw 353 actuates the wires 306 for the wrist unit 330 and the primary lead screw 343 moves the secondary cylinder 355 axially thereby actuating one of the secondary backbones 314. The secondary backbone 314 is operably coupled (e.g., connected) to the external tube connector 351 while the flexible wire 306 passes through this tube and is operably coupled connected to the secondary piston. By so arranging three of these 2 degree of freedom actuation units 371 around one central cylinder 360 used to actuate the gripper, there is yielded a seven (7) degree of freedom actuation unit 308 that is capable of actuating one distal dexterity device 300. The particular arrangement of these units with respect to each other is further illustrated in FIGS. 8 and 9.

As indicated herein, the distal dexterity apparatus 200 of the present invention includes one or more device manipulation units 206 that are operable coupled or mounted to the rotating base member 204, where there is one device manipulating unit 206 for each distal dexterity device 300 of the distal dexterity apparatus 200. In more particular embodiments, each device manipulating unit 206 is configured and arranged so as to control the position of a long axis of the associated distal dexterity device 300 with respect to the rotating base member 204. In preferred embodiments, each device manipulating unit 206 is configured and arranged so the distal dexterity device 200, including the portion containing the wrist unit 330, is capable of exhibiting one (1) or more degrees of freedom, more particularly a plurality or more of degrees of freedom and more specifically four (4) degrees of freedom and so as to control one or more of the angle of approach, the rotation about and the position along the long axis of the distal dexterity device 300 about an axis of rotation.

Figure 11:
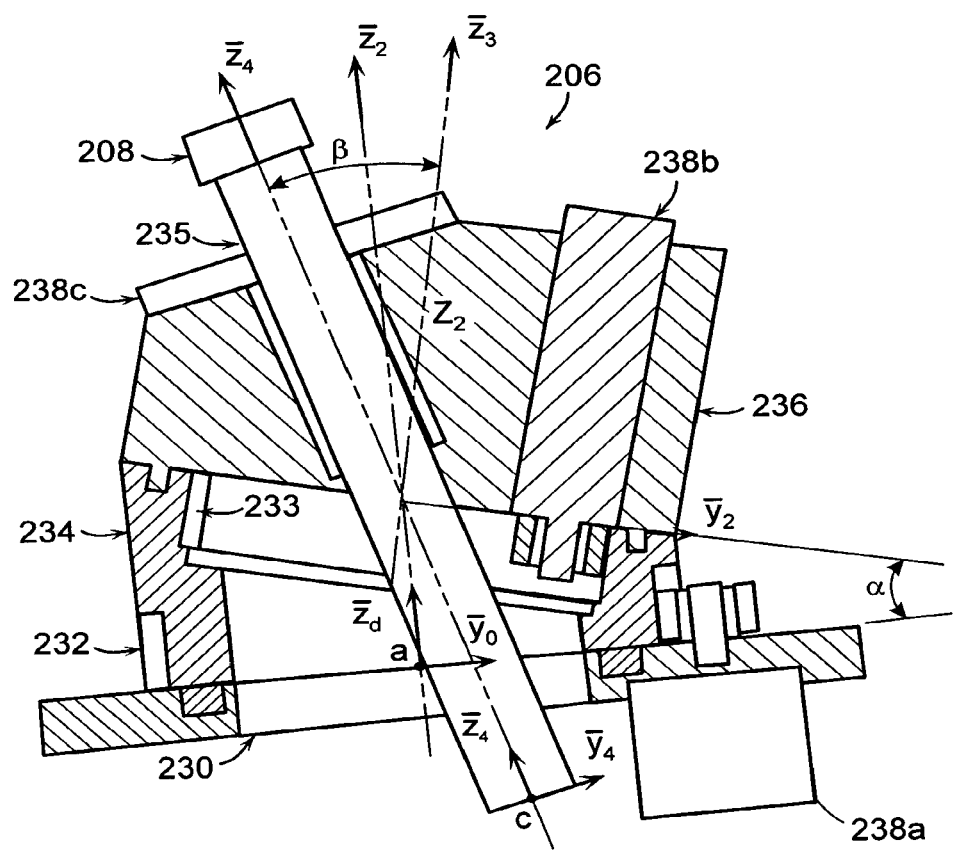
FIG. 11 is a side sectional view of a mechanism for setting the location and orientation of the distal dexterity device end portion.

Now referring to FIG. 11, there is shown an exemplary embodiment of a device manipulating unit 206 according to the present invention and more particularly there is shown a double cone mechanism that is used to set the location and orientation of the operable end 304 of the distal dexterity device when it is inserted into the throat. The additional third and fourth degree of freedom that is controlled by this double cone mechanism of the device manipulation device 206 are the axial motion of the distal dexterity device (e.g., in a direction in in/out of the throat) and rotation of the distal dexterity device, more specifically rotation of the manipulation device 310 thereof, about its longitudinal or long axis. Preferably the device manipulation unit 206 holds the minimally invasive surgical tool in the vicinity of the region to be subjected to operation procedures such as removal of tumors, polyps, or sewing (suturing).

The device manipulating unit 206 configured as a double cone mechanism includes a base member 230, a lower cone 232 having an outer gear ring 234 attached to it, and an upper cone 236. The lower cone 232 is capable of rotating about its axis, $\check{Z}_0$, and is driven by a motor 238$a$ that is mounted on the base member 230. The upper cone 236 is a driven by another motor, 238$b$, mounted on it and has a pinion meshing with an internal gear 233 fixed on the lower cone 232. The upper cone 236 is constrained only to rotate about its axis, $\check{Z}_3$, which is perpendicular to the plane of the lower cone 232. The upper cone 236 supports the guiding tube 235 that can rotate about its longitudinal axis relative to it. The guiding tube 235 passes through a linear spline joint, which is rotated by another motor 238$c$ that is mounted on the upper cone 236. The guiding tube 235 is equipped with a fast clamping/releasing device 208, that allows the surgeon to roughly adjust the axial location of the operable end 304 of the distal dexterity device 300 with respect to the surgical site (e.g., in the throat close to the region of interest). By using the rotation of the, upper and lower cones 232, 236 and the rotation of the guiding tube 235 about its axis one can control the orientation of the guiding tube in space. The fourth degree of freedom is controlled by a fourth motor and a wire mechanism moving the guiding tube 235 back and forth along its longitudinal axis (e.g., in a direction in/out of the throat). The figure illustrates the device manipulation unit 206 mechanism in its home position and so all the rotations of the upper cone and lower cone 232, 236 are measured from this position.

Figure 12:
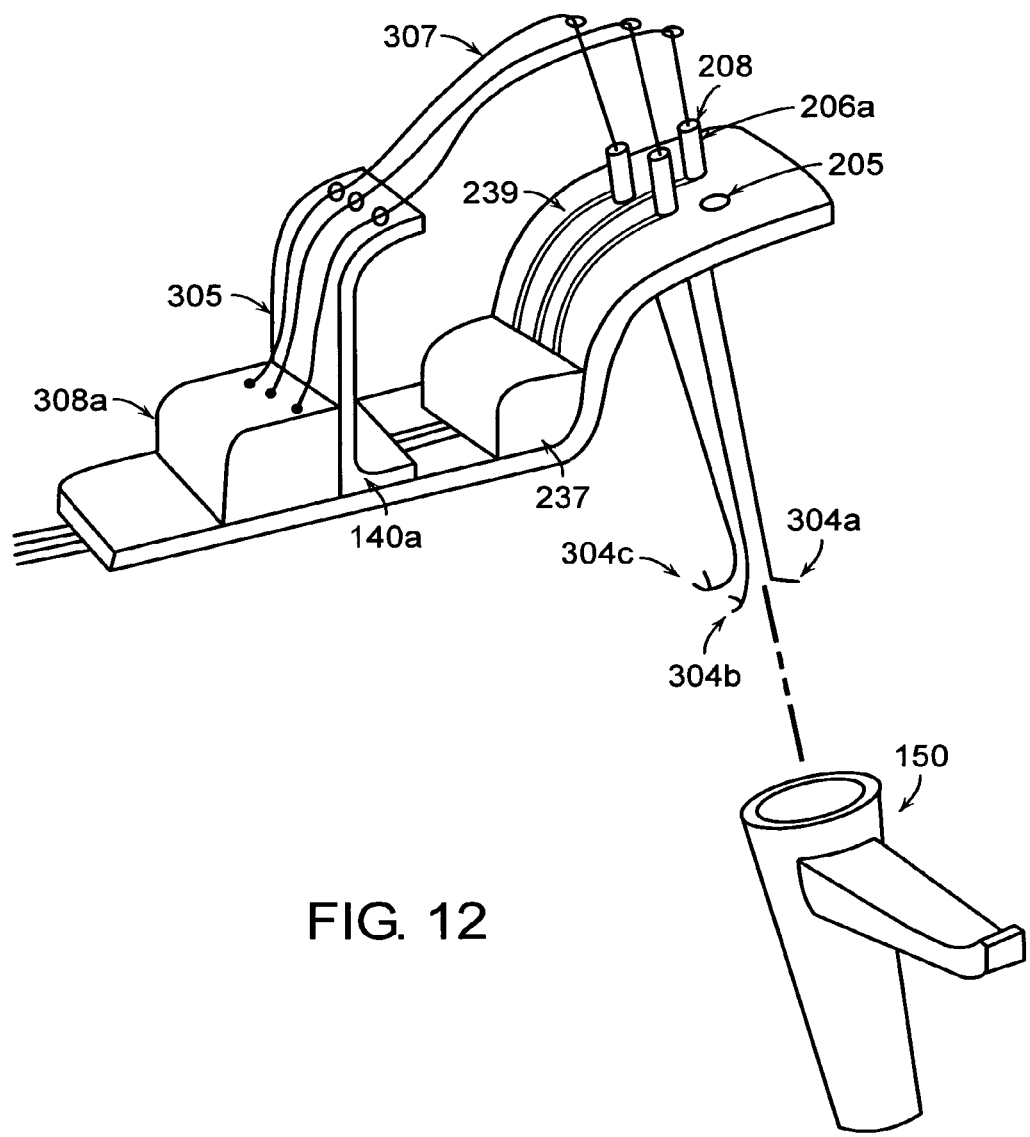
FIG. 12 is a schematic view of the distal dexterity apparatus according to another aspect of the present invention with the rotating member removed for clarity.

In the above discussion, the actuation units 308 of each distal dexterity unit 300 are illustrated as being attached to the holder member 302 and the device manipulation units 206 of the distal dexterity apparatus 200 are illustrated as having the drive units or motors thereof integrated with the device manipulation unit and thus mounted upon the rotating member 204. This, however, shall not be construed as a limitation on the scope of the present invention. As shown in the schematic view of FIG. 12, according to another aspect of the present invention, it is contemplated that an actuation unit 308a be located on the support 140a remote from the location of the holder members 302 and the device manipulation units 206. In the illustrated embodiment, actuation cables, disposed within a flexible actuation channels, operably couple the actuation unit 308a with each of the secondary backbones 314 and the wires 306 as herein described.

According to this aspect, a drive unit 237 for the drive manipulation device 206a is located on the support 140a and is operably coupled to a device manipulation device 206a remote from the location of the holder members 302 and the device manipulation units 206. In the illustrated embodiment, the flexible drive shafts 239 operably couple the drive unit 237 with each of the drive manipulation units 206 thereby providing the motive power for any of the drive manipulation devices 206a to act on the corresponding distal dexterity device 300 more particularly the holder member 302 thereof.

As indicated herein it is contemplated that a distal dexterity device 300 of the present invention be adapted so as to be capable of delivering therapeutics or therapeutic mediums to the treatment site. In addition, it also is contemplated that contrasting mediums or agents also can be delivered to the treatment site to facilitate any imaging of the treatment site following or during the surgical/ treatment procedure/ technique. As used herein therapeutic or therapeutic medium shall be understood to encompass or include, but are not limited to drugs, medicaments, antibiotics, antibacterials, antiproliferatives, neuroprotectives, anti-inflammatories (steroidal and non-sterodial), growth factors, neurotropic factors, antiangiogenics, thromobolytics, genes, nucleic acid molecules including encoding different types of nucleic acid molecules, an angiogenic factor, a growth factor, a chemotherapeutic agent, a radionuclide, a protein, a polypetide, a peptide, a viral protein, a lipid, an amphiphile, a nuclease inhibitor, a polymer, a toxin, a cell, and modified forms and combinations thereof that are used in therapeutic procedures in connection with the injury, insult, trauma or ischemia to the tissues or cells of the target or treatment site.

Exemplary therapeutic mediums include, but are not limited to, thrombin inhibitors; antithrombogenic agents; thrombolytic agents; fibrinolytic agents; vasospasm inhibitors; calcium channel blockers; vasodilators; antihypertensive agents; antimicrobial agents, such as antibiotics (such as tetracycline, chlortetracycline, bacitracin, neomycin, polymyxin, gramicidin, cephalexin, oxytetracycline, chloramphenicol, rifampicin, ciprofloxacin, tobramycin, gentamycin, erythromycin, penicillin, sulfonamides, sulfadiazine, sulfacetamide, sulfamethizole, sulfisoxazole, nitrofurazone, sodium propionate), antifungals (such as amphotericin B and miconazole), and antivirals (such as idoxuridine trifluorothymidine, acyclovir, gancyclovir, interferon); inhibitors of surface glycoprotein receptors; antiplatelet agents; antimitotics; microtubule inhibitors; anti-secretory agents; active inhibitors; remodeling inhibitors; antisense nucleotides; anti-metabolites; antiproliferatives (including antiangiogenesis agents); anticancer chemotherapeutic agents; anti-inflammatories (such as hydrocortisone, hydrocortisone acetate, dexamethasone 21-phosphate, fluocinolone, medrysone, methylprednisolone, prednisolone 21-phosphate, prednisolone acetate, fluoromethalone, betamethasone, triamcinolone, triamcinolone acetonide); non-steroidal anti-inflammatories (such as salicylate, indomethacin, ibuprofen, diclofenac, flurbiprofen, piroxicam); antiallergenics (such as sodium chromoglycate, antazoline, methapyriline, chlorpheniramine, cetrizine, pyrilamine, prophenpyridamine); anti-proliferative agents (such as 1,3-cis retinoic acid); decongestants (such as phenylephrine, naphazoline, tetrahydrazoline); miotics and anti-cholinesterase (such as pilocarpine, salicylate, carbachol, acetylcholine chloride, physostigmine, eserine, diisopropyl fluorophosphate, phospholine iodine, demecarium bromide); antineoplastics (such as carmustine, cisplatin, fluorouracil); immunological drugs (such as vaccines and immune stimulants); hormonal agents (such as estrogens, estradiol, progestational, progesterone, insulin, calcitonin, parathyroid hormone, peptide and vasopressin hypothalamus releasing factor); immunosuppressive agents, growth hormone antagonists, growth factors (such as epidermal growth factor, fibroblast growth factor, platelet derived growth factor, transforming growth factor beta, somatotropin, fibronectin); inhibitors of angiogenesis (such as angiostatin, anecortave acetate, thrombospondin, anti-VEGF antibody); dopamine agonists; radiotherapeutic agents; peptides; proteins; enzymes; extracellular matrix components; ACE inhibitors; free radical scavengers; chelators; antioxidants; anti-polymerases; photodynamic therapy agents; gene therapy agents; and other therapeutic agents such as prostaglandins, antiprostaglandins, prostaglandin precursors, and the like.

Antiproliferatives include any of a number of compounds, agents, therapeutic mediums or drugs known to those skilled in the art that inhibit the proliferation of cells. Such compounds, agents, therapeutic mediums or drugs include, but are not limited to, 5-fluorouracil, taxol, rapamycin, mitomycin C and cisplatin.

Neuroprotectives include any of a number of compounds, agents, therapeutic mediums or drugs known to those skilled in the art that guard or protect against neurotoxicity; the quality of exerting a destructive or poisonous effect upon nerve tissue. Such compounds, agents, therapeutic mediums or drugs include, but are not limited to, lubezole.

Anti-inflammatories include any of a number of compounds, agents, therapeutic mediums or drugs known to those skilled in the art, either steroidal or non-steroidal, and generally characterized as having the property of counteracting or suppressing the inflammatory process. Non-steroidal inflammatory drugs or compounds comprise a class of drugs which shares the property of being analgesic, antipyretic and antiinflammatory by way of interfering with the synthesis of prostaglandins. Such non-steroidal anti-inflammatories include, but are not limited to, indomethacin, ibuprofen, naxopren, piroxicam and nabumetone.

Anti-inflammatory steroids include triamcinolone acetonide, corticosteroids such as, for example, triamcinolone, dexamethasone, fluocinolone, cortisone, prednisolone, flumetholone, and derivatives thereof.

As is known to those skilled in the art, growth factors is a collective term originally used to refer to substances that promote cell growth and is now loosely used to describe molecules that function as growth stimulators (mitogens) but also as growth inhibitors (sometimes referred to as negative growth factors), factors that stimulate cell migration, or as chemotactic agents or inhibit cell migration or invasion of tumor cells, factors that modulate differentiated functions of cells, factors involved in apoptosis, factors involved in angiogenesis, or factors that promote survival of cells without influencing growth and differentiation.

As is known to those skilled in the art, neurotropic factors is a general term used to describe growth factors and cytokines that can enhance neuronal survival and axonal growth and that regulate synaptic development and plasticity in the nervous system. In the present invention, such growth factors include, but are not limited to, ciliary neurotrophic factors and brain-derived neurotrophic factors.

Antiangiogenics include any of a number of compounds, agents, therapeutic mediums or drugs known to those skilled in the art that inhibit the growth and production of blood vessels, including capillaries.

Thrombolytics, as is known to those skilled in the art include any of a number of compounds, agents, therapeutic mediums or drugs that dissolve blot clots, or dissolve or split up a thrombus.

It also shall be understood to include, composition thereof including a pharmaceutically acceptable carrier. For example, a carrier that is non-toxic, isotonic, hypotonic or weakly hypertonic and has a relatively low ionic strength (e.g., such as a sucrose solution). Furthermore, the composition may contain any relevant solvents, aqueous or partly aqueous liquid carriers comprising sterile, pyrogen-free water, dispersion media, coatings, and equivalents, or diluents (e.g. Tris-HCI, acetate, phosphate), emulsifiers, solubilizers and/or adjuvants. The pH of the pharmaceutical preparation is suitably adjusted and buffered in order to be appropriate for use in humans or animals. Representative examples of carriers or diluents for an injectable-composition include water or isotonic saline solutions which are preferably buffered at a physiological pH (e.g., such as phosphate buffered saline, Tris buffered saline, mannitol, dextrose, glycerol containing or not polypeptides or proteins such as human serum albumin). The compositions also can comprise one or more accessory molecules for facilitating the introduction of a nucleic acid delivery vector into a cell and/or for enhancing a particular therapeutic effect.

Prototype Experiment

A prototype of the manipulation device 310 of the present invention was developed and tested. The manipulation device 310 had a length of 28 mm and a diameter of 4.2 mm. It is designed to bend ±90° in any direction. The primary and secondary backbones 312, 314 are made of super elastic NiTi tubes having 0.66 and 0.5 mm external and internal diameters. All the disks comprising the base member, the intermediate spacer members and the end member 316, 320, 320 have a diameter of 4.2 mm and 1.6 mm thickness.

Figure 13A:
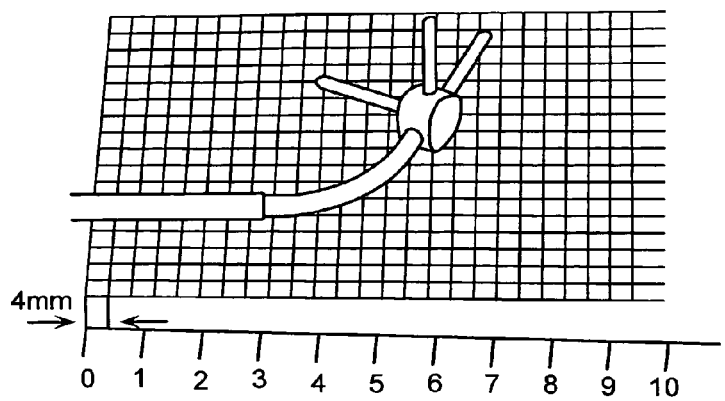
FIGS. 13A-C are illustrative views showing bending of a prototype of the manipulation device of the present invention.
Figure 13B:
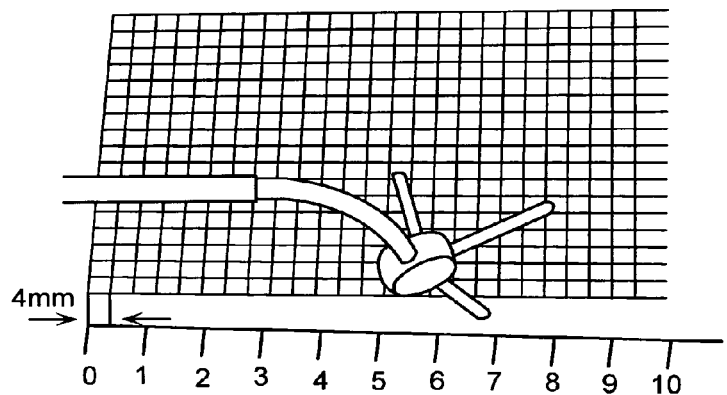
Figure 13C:
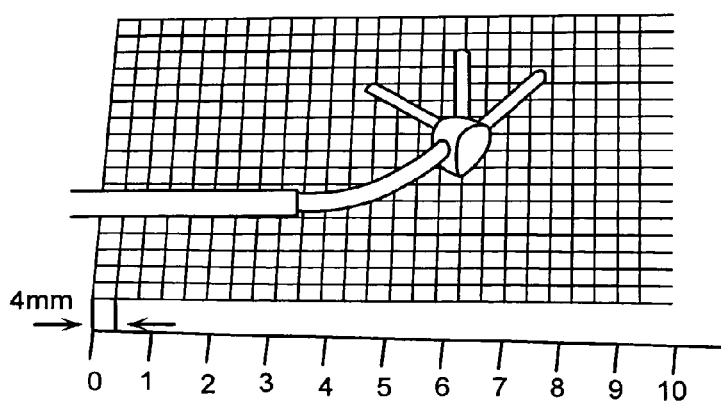

The prototype manipulation device was manually actuated using two out of the three secondary backbones 314 and was able to apply a force of more than 1 newton at its tip and was capable of bending the device so as to exhibit the two degrees of freedom and bending at an angle up to at least ±70° in any direction as illustrated in FIGS. 13A-C. In the design a design goal was followed such that the strain in the tubes does not exceed 4%. This strain limit is used to prevent degradation of the superelastic properties of the tubes over continuous operation. In actual use, all three secondary backbones would be actuated and by doing so it will demonstrate better load sharing among the backbones and thus we will be able to bend it further without violating the strain limit. The prototype served as an experimental setup for determining fatigue resilience and additional design parameters such as the maximal distance between the spacer disks to prevent buckling.

Although a preferred embodiment of the invention has been described using specific terms, such description is for illustrative purposes only, and it is to be understood that changes and variations may be made without departing from the spirit or scope of the following claims.

Incorporation By Reference

All patents, published patent applications and other references disclosed herein are hereby expressly incorporated by reference in their entireties by reference.

Equivalents

Those skilled in the art will recognize, or be able to ascertain using no more than routine experimentation, many equivalents of the specific embodiments of the invention described herein. Such equivalents are intended to be encompassed by the following claims.

What is claimed is:

1. A distal dexterity apparatus, comprising:
    a plurality of distal dexterity devices, each of the plurality of distal dexterity devices having a flexible manipulation device and an associated tool operably coupled to the flexible manipulation device, each flexible manipulation device being configured and arranged so as to maneuver the associated tool in one or more directions;
    a rotating base member configured and arranged to rotate about a first axis of rotation, wherein each of the plurality of dexterity devices is operably coupled to the rotating base member so that a long axis of each of the plurality of distal dexterity devices is essentially parallel to the first axis of rotation, rotation of the rotating base member about the first axis causing an operable end of each of the plurality of distal dexterity devices to rotate about the first axis of rotation; and
    an actuation device that is operably coupled to each flexible manipulation device, wherein the actuation device is configured and arranged so as to cause each flexible manipulation device to maneuver the associated tool in one or more directions responsive to outputs of the actuation device;
    wherein each flexible manipulation device includes:
        a base member;
        an end member proximal of the tool;
        one or more intermediate spacer members;
        a first axially extending member that is secured to each of the base member, the end member, and the or each of the intermediate spacer members; and
        one or more second axially extending members, the or each second axially extending members being a flexible tubular member having an internal actuator wire operably coupled to maneuver the associated tool, the flexible tubular member being secured to the end member and slidably disposed through an aperture in the or each of the intermediate spacer members and an aperture in the base member.

2. The distal dexterity apparatus of claim 1, wherein each flexible manipulation device is configured and arranged so as to be capable of two degrees of freedom when acted upon by the actuation device.

3. The distal dexterity apparatus of claim 1, wherein the actuating device is operably coupled to the or each of the second axially extending members and is configured and arranged so as to impose one of a pushing or pulling force on each of the second axially extending members so as to correspondingly push or pull against the end member causing at least one of the flexible manipulation devices to be manipulated.

4. The distal dexterity apparatus of claim 1, further comprising a device manipulation unit operably coupled to at least one of the plurality of distal dexterity devices so as to cause at least one of axial movement of the or each distal dexterity device along a long axis or rotation of the or each distal dexterity device about the long axis.

5. The distal dexterity apparatus of claim 1, wherein there are three second axially extending members that are disposed about and parallel to the first axially extending member, and wherein the first axially extending member is centrally located within the three second axially extending members.

6. The distal dexterity device of claim 1, further comprising:
   a moveable unit configured to operably couple to the tool; and
   a coupling device that operably couples the moveable unit to the actuation device;
   wherein the actuation device is configured and arranged to move the moveable unit with respect to the end member.

7. The distal dexterity device of claim 6, wherein the coupling device comprises one or more actuating members, the or each actuating member being operably coupled to the actuation device and to the moveable unit.

8. The distal dexterity device of claim 7, wherein the one or more actuating members and the moveable unit are each configured and arranged so that the moveable unit is removably operably coupled to the or each actuating member.

9. The distal dexterity device of claim 6, wherein the coupling device and the moveable unit are configured and arranged so that the moveable unit is removably operably coupled to the coupling device.

10. The distal dexterity apparatus of claim 1, wherein each of the first and second axially extending members includes a lumen.

11. The distal dexterity device of claim 1, further comprising:
   a device manipulation unit operably coupled to at least one of the plurality of distal dexterity devices and to the rotating base member, the device manipulation unit being configured and arranged so as to cause at least one of axial movement of the or each distal dexterity device along a long axis or rotation of the or each distal dexterity device about a second axis of rotation different from the long axis.

12. The distal dexterity apparatus of claim 1, wherein the plurality of distal dexterity devices are arranged in series.

13. The distal dexterity apparatus of claim 1, wherein the actuation device is configured and arranged to apply a linear force on the or each of the second axially extending members.

14. The distal dexterity apparatus of claim 1, wherein the actuation device is configured and arranged to apply at least one of a push or a pull force on the or each of the second axially extending members.

15. The distal dexterity apparatus of claim 1, wherein for at least one of the plurality of distal dexterity devices, the associated tool is removably operably coupled to the end member so as to extend outwardly from an end of the flexible manipulation device.

16. The distal dexterity apparatus of claim 1, wherein the or each flexible tubular member comprises a super-elastic material.

17. A method for performing minimally invasive diagnostic, surgical, or therapeutic techniques, the method comprising:
   providing a distal dexterity apparatus having a plurality of distal dexterity devices, an actuation device, and a rotating base member configured and arranged to rotate about a first axis of rotation, wherein each of the plurality of distal dexterity devices is operably coupled to the rotating base member so that a long axis of each of the plurality of distal dexterity devices is essentially parallel to the first axis of rotation, rotation of the rotating base member about the first axis causing an operable end of each of the plurality of distal dexterity devices to rotate about the first axis of rotation,
   each of the plurality of distal dexterity devices having a flexible manipulation device and an associated tool operably coupled to the flexible manipulation device, each flexible manipulation device being configured and arranged so as to maneuver the associated tool in one or more directions,
   the actuation device operably coupled to each flexible manipulation device and configured and arranged to cause each flexible manipulation device to maneuver the associated tool in one or more directions responsive to one or more outputs of the actuation device,
   the flexible manipulation device including a base member, an end member, one or more intermediate spacer members, a first axially extending member, and one or more second axially extending members,
   the end member proximal of the tool,
   the first axially extending member being secured to each of the base member, to the end member, and to the or each intermediate spacer member,
   the or each second axially extending member being a flexible tubular member having an internal actuator wire operably coupled to maneuver the associated tool,
   the or each flexible tubular member being secured to the end member and slidably disposed through an aperture in the or each of the intermediate spacer members and an aperture in the base member; and
   causing the tool to move by actuation of the actuation device.

18. The method of claim 17, wherein each distal dexterity apparatus further comprises a device manipulation unit operably coupled to the distal dexterity devices and to the rotating base member, the device manipulation unit being configured and arranged so as to cause one of axial movement of the distal dexterity device along a long axis of the distal dexterity device or rotation of the distal dexterity device about a second axis of rotation.

19. The method of claim 17, wherein the plurality of distal dexterity devices are arranged in series.

20. The method of claim 17, wherein the or each flexible tubular member comprises a super-elastic material.

* * * * *